(12) United States Patent
Lawton et al.

(10) Patent No.: US 6,504,013 B1
(45) Date of Patent: Jan. 7, 2003

(54) CANINE ALLERGY THERAPEUTIC RECOMBINANT CHIMERIC ANTI-IGE MONOCLONAL ANTIBODY

(75) Inventors: Robert L. Lawton, Gorham, ME (US); Ashok P. Aiyappa, Scarborough, ME (US); Wendy W. Liu, Shaker Heights, OH (US); Brion Mermer, Cumberland, ME (US); Hongliang Guo, Scarborough, ME (US); Eugene R. Krah, III, Portland, ME (US)

(73) Assignee: Idexx Laboratories, Inc., Westbrook, ME (US)

( * ) Notice: Subject to any disclaimer, the term of this patent is extended or adjusted under 35 U.S.C. 154(b) by 23 days.

(21) Appl. No.: 09/592,998

(22) Filed: Jun. 12, 2000

Related U.S. Application Data
(60) Provisional application No. 60/179,629, filed on Feb. 1, 2000.

(51) Int. Cl.[7] .................................................. C12P 21/08
(52) U.S. Cl. .................................. 530/387.3; 424/141.1
(58) Field of Search ..................... 424/141.1; 530/387.3

(56) References Cited

U.S. PATENT DOCUMENTS

| | | | |
|---|---|---|---|
| 5,422,258 A | 6/1995 | Chang | 435/172.2 |
| 5,543,144 A | 8/1996 | Chang | |
| 5,629,415 A | 5/1997 | Hollis et al. | 536/23.53 |
| 5,653,980 A | 8/1997 | Hellman | 424/184.1 |
| 5,945,294 A | 8/1999 | Glenn et al. | |
| 5,965,709 A | 10/1999 | Presta et al. | 530/387.3 |
| 5,994,511 A | 11/1999 | Lowman et al. | 530/387.3 |
| 6,060,326 A * | 5/2000 | Frank et al. | |

FOREIGN PATENT DOCUMENTS

| | | | |
|---|---|---|---|
| EP | 0957111 | * | 9/1999 |
| EP | 0957111 | | 11/1999 |
| WO | WO 89 06138 | | 7/1989 |
| WO | WO 93/04173 | * | 3/1993 |
| WO | WO 94 20533 | | 9/1994 |
| WO | 9720859 | | 6/1997 |
| WO | 9845707 | | 10/1998 |
| WO | WO 99 67293 | | 12/1999 |

OTHER PUBLICATIONS

Janewray et al ImmunoBiology pp. 316–318, 1994.*
Deboer et al., "Production and Characterization of Mouse Monoclonal Antibodies Directed Against Canine IgE and IgE" Vet. Immunol. Immunopathol. 37:183–199 (1993).
Kurumi et al. "DNA Sequences Coding for Unchangeable Region of Dog Immunoglobulin Gamma Chain" EMBL E03345. Oct. 8, 1997, updated Sep. 2, 2000.
International Search Report for PCT/US 01/02924 corresponding to the pending application.

* cited by examiner

*Primary Examiner*—Patrick J. Nolan
*Assistant Examiner*—Gerald R. Ewoldt
(74) *Attorney, Agent, or Firm*—McDonnell Boehnen Hulbert & Berghoff

(57) ABSTRACT

The present invention provides methods and compositions for decreasing IgE levels in dogs. The methods and compositions are useful for treating allergic symptoms in dogs. The invention may comprise chimeric canine anti-IgE monoclonal antibody compositions and methods for using the compositions in the treatment of allergy. In preferred embodiments, the compositions of the present invention may act by binding soluble IgE in plasma, or by inhibiting IgE from binding to receptors on mast cells, B cells, and basophils.

1 Claim, 14 Drawing Sheets

| DOG ID | WEIGHT (g) | BLOOD VOL. (ml) | IgE LEVEL (ug/ml) | TOTAL FREE IgE (mg) | 10X c15A2 (mg) |
|---|---|---|---|---|---|
| 2002 | 9,300g | 558 ml | 1.61 | 0.898mg | 8.98mg |
| 2003 | 12,200g | 732ml | 9.71 | 7.11mg | 71.1mg |
| 2103 | 8,000g | 480ml | 8.14 | 3.91mg | 39.1mg |
| TOTAL | | | | | 119.18mg |

** DOG BLOOD VOLUME: 6% OF BODY WEIGHT

```
                M   P   A   S     M   G   G   P     A   L   L     W   L   A
5401  CCGCGAGATG CCTGCTTCCA TGGGAGGCCC TGCCCTGCTG TGGCTAGCGC
      GGCGCTCTAC GGACGAAGGT ACCCTCCGGG ACGGGACGAC ACCGATCGCG

L   L   L   S       S   P   G     V   M   S     S   D   T   L     K   P   T
5451  TGCTGCTCTC CTCTCCAGGT GTCATGTCAT CAGATACCTT GAAACCTACA
      ACGACGAGAG GAGAGGTCCA CAGTACAGTA GTCTATGGAA CTTTGGATGT

V   S   M     N   P   P   W     N   T   I     L   K   D     D   S   V   T
5501  GTGTCCATGA ACCCGCCATG GAATACAATA TTGAAGGATG ACAGTGTGAC
      CACAGGTACT TGGGCGGTAC CTTATGTTAT AACTTCCTAC TGTCACACTG

L     T   C     T   G   N       N   S   L   E     V   D   S     A   V   W
5551  TCTTACATGT ACTGGGAACA ACTCCCTTGA AGTCGACTCT GCTGTGTGGC
      AGAATGTACA TGACCCTTGT TGAGGGAACT TCAGCTGAGA CGACACACCG

L   H   N   N     T   T   W     Q   E   T     T   S   R   L     D   I   N
5601  TCCACAACAA CACTACTTGG CAAGAGACGA CTTCACGTTT GGACATCAAT
      AGGTGTTGTT GTGATGAACC GTTCTCTGCT GAAGTGCAAA CCTGTAGTTA

K   A   Q     I   Q   D   S       G   E   Y     R   C   R     E   N   R   S
5651  AAAGCCCAAA TCCAGGACAG TGGGAGTAC AGGTGTCGGG AAAATAGATC
      TTTCGGGTTT AGGTCCTGTC ACCCCTCATG TCCACAGCCC TTTTATCTAG
```

*FIG. 10A*

```
          I   L   S   D   P   V   Y   L   T   V   F   T   E   W   L   I
5701  CATCCTGAGT GATCCTGTGT ACCTAACAGT CTTCACAGAG TGGCTGATCC
      GTAGGACTCA CTAGGACACA TGGATTGTCA GAAGTGTCTC ACCGACTAGG

L   Q   A   S   A   N   V   V   M   E   G   E   S   F   L   I   R
5751  TTCAAGCCTC TGCCAACGTG GTGATGGAGG GTGAGAGCTT CCTCATCAGG
      AAGTTCGGAG ACGGTTGCAC CACTACCTCC CACTCTCGAA GGAGTAGTCC

C   H   S   W   K   N   L   R   L   T   K   V   T   Y   Y   K   D
5801  TGCCATAGTT GGAAGAATTT GAGGCTCACA AAGGTGACCT ACTACAAGGA
      ACGGTATCAA CCTTCTTAAA CTCCGAGTGT TTCCACTGGA TGATGTTCCT

G   I   P   I   R   Y   W   Y   E   N   F   N   I   S   I   S
5851  TGGCATCCCC ATCAGGTACT GGTACGAGAA CTTCAACATC TCCATTAGCA
      ACCGTAGGGG TAGTCCATGA CCATGCTCTT GAAGTTGTAG AGGTAATCGT

N   V   T   K   N   S   G   N   Y   S   C   S   G   Q   I   Q
5901  ACGTCACAAC CAAAAACAGC GGCAACTATT CCTGCTCAGG CCACATCCAG
      TGCAGTGTTG GTTTTTGTCG CCGTTGATAA GGACGAGTCC GGTCTAGGTC

Q   K   G   Y   T   S   K   V   L   N   I   I   V   K   K   E   P
5951  CAGAAAGGCT ACACCTCTAA AGTCCTCAAC ATTATTGTGA AAAAGAGCC
      GTCTTTCCGA TGTGGAGATT TCAGGAGTTG TAATAACACT TTTTTCTCGG
```

*FIG. 10B*

```
         T   K   Q     N   K   Y     S   G   L   H     R   P   P     D   C   P
6001  CACCAAGCAA AACAAGTACT CCGGGCTACA CCGCCCACCT GATTGTCCCA
      GTGGTTCGTT TTGTTCATGA GGCCCGATGT GGCGGGTGGA CTAACAGGGT

K   C   P   A     P   E   M     L   G   G     P   S   V   F     I   F   P
6051  AATGCCCAGC CCCTGAAATG CTGGGAGGGC CTTCGGTCTT CATCTTTCCC
      TTACGGGTCG GGGACTTTAC GACCCTCCCG GAAGCCAGAA GTAGAAAGGG

P   K   P     K   D   T   L     L   I   A     R   T   P     E   V   T   C
6101  CCGAAACCCA AGGACACCCT CTTGATTGCC CGAACACCTG AGGTCACATG
      GGCTTTGGGT TCCTGTGGGA GAACTAACGG GCTTGTGGAC TCCAGTGTAC

V   V   V     D   L   D     P   E   D   P     E   V   Q     I   S   W
6151  TGTGGTGGTG GATCTGGACC CAGAAGACCC TGAGGTGCAG ATCAGCTGGT
      ACACCACCAC CTAGACCTGG GTCTTCTGGG ACTCCACGTC TAGTCGACCA

F   V   D   G     K   Q   M     Q   T   A     K   T   Q   P     R   E   E
6201  TCGTGGACGG TAAGCAGATG CAAACAGCCA AGACTCAGCC TCGTGAGGAG
      AGCACCTGCC ATTCGTCTAC GTTTGTCGGT TCTGAGTCGG AGCACTCCTC

Q   F   N     G   T   Y   R     V   V   S     D   L   P     I   G   H   Q
6251  CAGTTCAATG GCACCTACCG TGTGGTCAGT GACCTCCCCA TTGGGCACCA
      GTCAAGTTAC CGTGGATGGC ACACCAGTCA CTGGAGGGGT AACCCGTGGT
```

*FIG. 10C*

```
        D   W   L     K   G   K     Q   F   T   C     K   V   N     N   K   A
6301    GGACTGGCTC    AAGGGGAAGC    AGTTCACCTG    CAAAGTCAAC    AACAAAGCCC
        CCTGACCGAG    TTCCCCTTCG    TCAAGTGGAC    GTTTCAGTTG    TTGTTTCGGG

L   P   S   P     I   E   R     T   I   S     K   A   R   G     L   A   I
6351    TCCCATCCCC    GATCGAGAGG    ACCATCTCCA    AGGCCAGAGG    GCTGGCCATA
        AGGGTAGGGG    CTAGCTCTCC    TGGTAGAGGT    TCCGGTCTCC    CGACCGGTAT

A   S   V     Y   V   L   P             P   S   R     E   E   L     S   K   N   T
                                        SmaI,XmaI,AvaI
6401    GCCAGTGTGT    ATGTCCTGCC    GCCATCCCGG    GAGGAGTTGA    GCAAGAACAC
        CGGTCACACA    TACAGGACGG    CGGTAGGGCC    CTCCTCAACT    CGTTCTTGTG

V   S   L     T   C   L     I   K   D   F     F   P   P     D   I   D
6451    AGTCAGCTTG    ACATGCCTGA    TCAAAGACTT    CTTCCCCCCT    GACATTGATG
        TCAGTCGAAC    TGTACGGACT    AGTTTCTGAA    GAAGGGGGGA    CTGTAACTAC

V   E   W   Q     S   N   G     Q   Q   E     P   E   S   K     Y   R   T
6501    TGGAGTGGCA    GAGCAATGGA    CAGCAGGAGC    CTGAGAGTAA    GTACCGCACG
        ACCTCACCGT    CTCGTTACCT    GTCGTCCTCG    GACTCTCATT    CATGGCGTGC

T   L   P     Q   L   D   E     D   G   S     Y   F   L     Y   S   K   L
6551    ACCCTGCCCC    AGCTGGACGA    GGACGGGTCC    TACTTCCTGT    ACAGCAAGCT
        TGGGACGGGG    TCGACCTGCT    CCTGCCCAGG    ATGAAGGACA    TGTCGTTCGA
```

*FIG. 10D*

```
          S   V   D       K   S   R       W   Q   R   G       D   T   F       I   C   A
6601  CTCTGTGGAT AAGAGCCGCT GGCAGCGGGG AGACACCTTC ATATGTGCGG
      GAGACACCTA TTCTCGGCGA CCGTCGCCCC TCTGTGGAAG TATACACGCC

V   M   H   E       A   L   H       N   H   Y       T   Q   K   S       L   S   H
6651  TGATGCATGA AGCTCTACAC AACCACTACA CACAGAAATC CCTCTCCCAT
      ACTACGTACT TCGAGATGTG TTGGTGATGT GTGTCTTTAG GGAGAGGGTA

CANINE ALLERGY THERAPEUTIC RECOMBINANT CHIMERIC ANTI-IGE MONOCLONAL ANTIBODY

This application claims benefit of priority to U.S. Provisional Application Ser. No. 60/179,629 filed on Feb. 1, 2000.

FIELD OF THE INVENTION

The present invention provides compositions and methods for decreasing IgE levels and for alleviating allergic symptoms in canines. The compositions comprise chimeric canine anti-IgE mAbs and the methods are useful for treating allergies in canines.

BACKGROUND ART

It is estimated that up to 30% of all dogs suffer from allergies or allergy-related skin disorders. Specifically, allergic dermatitis has been estimated to affect between 3% and 15% of the entire canine population. Given the prevalence of allergies in dogs, there is a need to develop methods and compositions to properly diagnose and treat, canine allergies.

The substances most likely to cause an allergic reaction vary from species to species. Common canine allergens include fleas, pollens, molds and dust. Allergy to fleas is believed to be the most common dog allergy. Typically, a flea's saliva is the allergen, and a single fleabite can cause substantial itching. An additional form of allergy in dogs is termed atopy. Atopy is a condition where a dog. is allergic to inhalants such as pollens, molds or microscopic mites found in house dust. Current treatments of canine allergies often focus on the use of steroids which cause undesirable side effects or allergen-mediated desensitization which requires a different treatment for each type of allergy.

In mammals, antibody molecules are classified into various isotypes referred to as IgA, IgD, IgE, IgG, and IgM. Antibody molecules consist of heavy and light chain components. The heavy chains of molecules of a given isotype have extensive regions of amino acid sequence homology, and conversely have regions of difference from antibodies belonging to other isotypes. The shared regions of the heavy chains provide members of each isotype with common abilities to bind to certain cell surface receptors or to other macromolecules such as complement, and therefore to activate particular immune effector functions. Accordingly, separation of antibody molecules into isotypes also serves to separate the antibodies according to a set of effector functions that they commonly activate. In humans and dogs, Immunoglobulin E (IgE) is involved in allergy, and recognizes antigen in immediate hypersensitivity reactions.

Furthermore, IgE is the antibody type that is understood to be an important mediator of allergic response in mammals, including Type I immediate hypersensitivity. IgE molecules bind to receptors on mediator cells such as mast cells. This binding occurs when the Fc region of the IgE molecule is bound to Fc receptors on the mast cells. When such cell-bound IgE antibodies then bind to an allergen, the allergen cross-links multiple IgE antibodies on the mast cell surface. This cross-linking mediates Type I immediate hypersensitivity reactions and causes release of histamines and other molecules that produce symptoms associated with allergy.

In humans the serum level of total IgE is diagnostic of allergic disease. To explore the possibility that the serum level of IgE might also be diagnostic of allergy in dogs, DeBoer and Hill performed additional studies. (Hill and DeBoer, Am. J. Vet. Res. 55 (7):944–48 (1994)). They used monoclonal antibody ("mAb") D9, in an ELISA assay with the following configuration: D9 was bound to a substrate, antibodies were captured by D9 and then D9 having a marker was used to flag the captured antibody.

The Hill and DeBoer ELISA was used to establish the total amount of IgE in canine serum in an effort to diagnose canine allergy. However, it was found that quantifying IgE was not useful for diagnosing allergy in dogs. (See, e.g., Abstract and Discussion sections of Hill and DeBoer.) This finding was in direct contrast to the situation in human immunology. This result points out the difficulty of any attempt to correlate data between animals of two different genera.

This difficulty is further exemplified by the fact that dogs can be allergic to a different set of antigens than humans are. Allergies to fleas, for instance, are a severe problem for dogs but not humans. Furthermore, in instances where dogs and humans appear to be allergic to the same allergen extract, studies by doctors Esch and Greer of Greer Laboratories (Lenoir, N.C.), have indicated that the specific allergens in an allergen extract which produce canine disease are not necessarily the same allergens that produce disease in humans. For example, it is known that the immunodominant components of dust mite extracts are different in dogs than in humans.

Adding to the difficulty of study across genera of allergic mechanisms and response is that allergies in dogs are primarily expressed in the skin, while humans primarily exhibit allergic symptoms in the respiratory system. Additionally, eosinophilia is correlated to allergies in humans, but not in dogs.

In considering the administration of a therapeutic composition to treat a physiological condition, when recombinant or chimeric molecules are administered in vivo to an animal, they may be quickly cleared from that animal. Recombinant IgG molecules have been used to increase the half-life of recombinant molecules when the recombinants are administered to an animal. E.g., Capon, D., Chamow, S., et al., "Designing CD4 immunoadhesins," Nature 337:525 (1989); Byrn, R., Mordenti, C., et al., "Biological Properties of a CD4 Immunoadhesin," Nature 344:667 (1990); Haak-Frendscho, M., Ridgway, J., et al., "Human IgE Receptor Alpha-Chain IgG Chimera Blocks Passive Cutaneous Anaphylaxis Reaction in vitro," Journal of Immunology 151:351–53 (1993); U.S. Pat. No. 5,116,964, issued May 26, 1992 to Capon, D. J., et al. entitled "Hybrid Immunoglobulins".

It is generally accepted that in humans IgG is the immunoglobulin isotype with the longest serum half-life. In dogs, the isotype with the longest half-life is not known. Although the sequences that are believed to correspond to a portion of exon 1 and 3 of at least two and possibly all four heavy chain canine IgG immunoglobulin sequences have been reported in U.S. Pat. No. 5,593,861 to Maeda et al., it is not known which of these heavy chain sequences is part of the IgG structure with the longest half-life in dogs.

IgE levels are elevated in human patients experiencing allergic disease, and IgE is believed to mediate allergic symptoms. Although the levels of serum IgE may not correlate with allergic disease in dogs, it may nevertheless be desirable to decrease IgE levels as a mechanism for alleviating allergic symptoms.

Furthermore, there is a need for compositions and methods for treatment of canine allergies which avoid the disadvantages of the conventional compositions and methods, yet provide effective treatment for canine allergies.

One object of the present invention is to provide compositions and methods for treatment of canine allergies, with substantially less side effects than those experienced with steroid treatments.

Another object of the invention is to provide compositions and methods of treatment for alleviating canine allergy symptoms that are effective independent of the type of allergen, and compositions and methods where treatment is based on the presence of an allergic response rather than a specific allergen.

Another object of the present invention is to provide compositions and methods of treatment for alleviating canine allergy symptoms by targeting IgE synthesis.

These and other objects will be apparent to those skilled in the art from the following disclosure and appended claims.

SUMMARY OF THE INVENTION

The present invention concerns compositions and methods for treating allergy in dogs. More particularly, the invention provides methods and compositions for administration to dogs, which compositions actually bind the dog's immunoglobulin E molecules so that the binding of free, serum IgE will inhibit this IgE from binding to the high affinity IgE receptor on mast cells and basophils. The compositions and methods provided may eliminate or reduce levels of free serum IgE. Lower free serum IgE levels may down regulate the synthesis and expression of the high affinity IgE receptor on basophils and mast cells. The result may be the reduction or elimination of free and/or total serum IgE and the reduction or elimination of the IgE response to allergen on skin mast cells. By "free serum IgE" is meant that IgE which is able to bind to the high affinity IgE receptor, and is unbound IgE in serum.

We have demonstrated that sustained elimination of detectable free and/or total serum IgE for 7 days and possibly a shorter time period results in a negative, feedback-loop that continues to suppress IgE synthesis. Sustained suppression of IgE synthesis will result in the elimination of a skin response to allergen.

In a preferred embodiment, the specificity and structure of a chimeric anti-IgE molecule of the present invention may allow for direct targeting of the IgE+ B cell. This binding may result in a reduction or elimination of IgE synthesis either through negative stimulation of the mature B cell or by destruction of the B cell by apoptosis or complement-mediated lysis.

The present invention may therefore comprise an IgE receptor molecule which comprises a chimera and which specifically binds to canine IgE. The receptor molecule may be an antibody molecule, preferably a monoclonal antibody ("mAb"), and the mAb may preferably have an affinity for exon 3 of canine IgE. The chimera may comprise canine and mouse immunoglobulin. The chimera may further comprise canine constant heavy and light domains fused to mouse heavy and light chain variable regions. The receptors and antibody molecules of the present invention may also comprise IgG heavy chain sequences.

The receptors and antibody molecules of the present invention may prevent binding of IgE to a second IgE receptor and the second IgE receptor may be located on one or more of a mast cell or basophil. The receptors and antibody molecules of the present invention may be comprised of protein, peptides, or other organic molecules.

The present invention also provides methods of treating canine allergies comprising administering to the canine a receptor or monoclonal antibody which comprises a chimera of the present invention and specifically binds to canine IgE. The methods of the present invention may result in a lowering of serum IgE levels in the treated canine, or in the binding of IgE on B cells and the subsequent elimination of clonal populations of B cells. The methods may also result in binding of serum IgE in plasma, or in an inhibition of IgE production in the treated canine. The lowering of serum IgE levels of the present methods may be caused by a disruption of blocking of interactions between IgE and receptors for IgE which may be located on mast cells or basophils.

The present invention further provides pharmaceutical formulations containing therapeutic amounts of the receptors of the present invention.

DESCRIPTION OF FIGURES

FIG. 10 depicts the DNA sequence (SEQ. ID NO:8) of the recombinant IgE receptor cRcIg with corresponding translation (SEQ. ID NO:9 and SEQ ID NO:10). The four additional amino acids at the bottom of the figure that lack the corresponding nucleotides are SEQ ID NO:10.

DETAILED DESCRIPTION OF THE INVENTION

Figure 1:
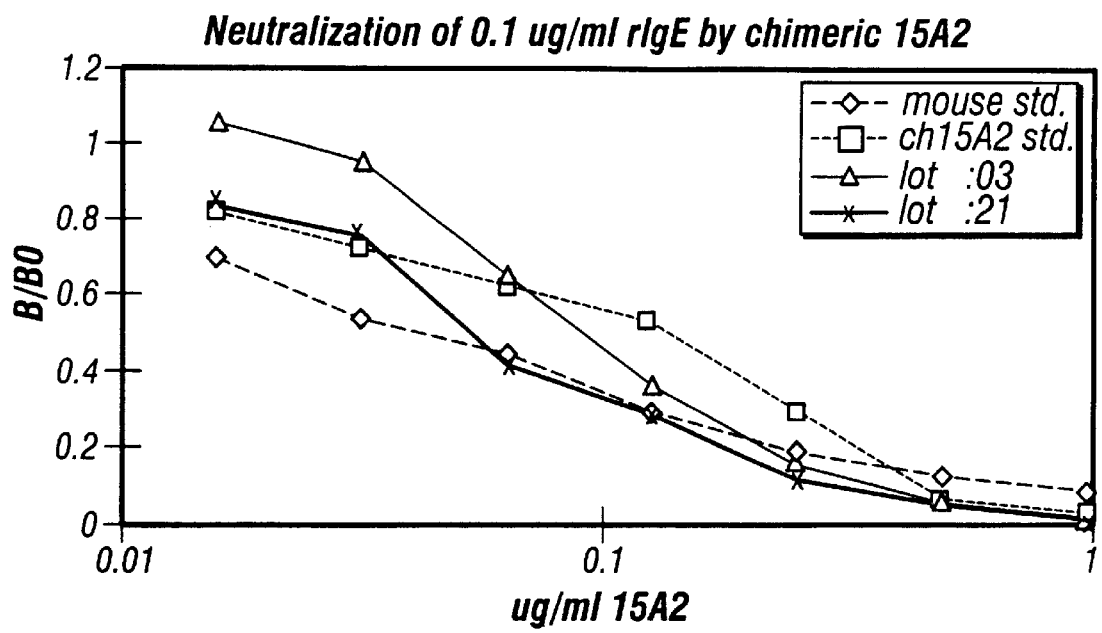
FIG. 1 depicts the ability of chimeric 15A.2 to inhibit IgE from binding to the recombinant canine IgE receptor.

Definitions:

Affinity: an attractive force or binding strength between a ligand and its receptor or between two binding moieties. Affinity also keeps the binding pair bound in equilibrium.

Amino acids: Organic molecules containing an amino group that can be combined in linear arrays to form polypeptides, peptides or proteins. The 20 common amino acids are alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. It will be recognized by those skilled in the art that in embodiments of the invention with conservative variants, any of the common amino acids, as well as others not listed, may be used in the present invention.

Canine IgE Receptor: A recombinant or chimeric receptor as defined herein, which exhibits affinity for canine IgE, or otherwise has the result of removing IgE from canine sera, in vivo or in vitro.

cDNA clone: A duplex DNA sequence representing an RNA, carried in a cloning vector.

Chimeric mAb: An immunoglobulin molecule with a hybrid amino acid sequence that has resulted from combining amino acids from at least two different canine Ig sources. Generally, the amino acid sequences are not normally found together in nature. "mAb" indicates monoclonal antibody.

Cloning vector: A plasmid, phage DNA or other DNA sequence, able to replicate in a host cell and capable of carrying exogenously added DNA sequence for purposes of amplification or expression of the added DNA sequence.

Conservative variant: Conservative variants of nucleotide sequences include nucleotide substitutions that do not result in changes in the amino acid sequence, as well as nucleotide substitutions that result in conservative amino acid substitutions, or amino acid substitutions which do not substantially affect the character of the polypeptide translated from said nucleotides. For example, polypeptide character is not substantially affected if the substitutions do not preclude specific binding of the peptide to canine IgE receptor or other canine IgE ligands.

Conservative variants of amino acid sequences include amino acid substitutions or deletions that do not substantially affect the character of the variant polypeptide relative to the starting peptide. For example, polypeptide character is not substantially affected if the substitutions or deletions do not preclude specific binding of the variant peptide to a specific binding partner of the starting peptide. Included in this definition are glycosylated and other variants and derivatives that will be apparent to those skilled in the art and are considered to fall within the scope of this invention. Also included in this definition are amino acid insertions, substitutions, deletions and truncations that do not substantially affect the polypeptide character relative to the starting peptide.

Expression control sequence: a DNA sequence of nucleotides that controls and regulates expression of structural genes when operatively linked to those genes.

Exon: A contiguous region of DNA encoding a portion of a polypeptide. Reference to any exon, e.g. "DNA sequence of exon 6", refers to the complete exon or any portion thereof.

Free IgE or Serum IgE: IgE in circulation in a patient not complexed or bound with a native or administered receptor having affinity for IgE or other IgE molecules.

Genome: The entire DNA of a substance. It includes, among other things, the structural genes encoding for the polypeptides of the substance, as well as operator, promoter and ribosome binding and interaction sequences such as the Shine-Dalgarno sequences.

Specific binding: Binding of one substance to another at greater binding affinity than background binding. Two substances that exhibit specific binding are referred to as specific binding partners, or as a specific binding pair. An antibody and its antigen are one example of a specific binding pair.

Structural gene: A DNA sequence that encodes through its template or messenger RNA ("mRNA") a sequence of amino acids characteristic of a specific polypeptide.

Therapeutic amount: A "therapeutic amount" is an amount of mAb that decreases serum IgE levels or suppresses IgE production or activity in the treated animal and has the effect of ameliorating or preventing symptoms of a disorder or physiological condition.

Total IgE: By "total IgE" is meant total serum IgE, whether bound or not by. another molecule.

As disclosed herein, a novel chimeric canine anti-IgE mAb was produced and administered to ragweed sensitized dogs. This chimeric molecule, designated c15A.2, consists of canine constant heavy and light domains fused to mouse heavy and light variable regions. In all cases, such administration led to a sustained decrease in circulating free IgE levels to below the level of detectability. In addition, total IgE, including that complexed with chimeric 15A.2 and still in circulation and detectable immediately after administration of c15A.2, was reduced over time. After 28 days of administration, free c15A.2 was detectable in serum, but both free and total serum IgE were undetectable. The use of a humanized anti-IgE monoclonal antibody as a therapeutic agent for human allergy was disclosed in U.S. Pat. No. 5,593,861 to Maeda et al. It is believed that IgE removal by administration of recombinant anti-IgE mAb has not previously been shown in dogs. The person of ordinary skill will realize that the present invention and the discussion herein pertaining to mAb is equally applicable to receptors which may comprise parts of antibody molecules. Therefore, the discussion herein is intended to relate to compositions of receptors, not solely antibodies.

The canine anti-IgE mAb compositions of the present invention may be recombinant or chimeric structures of canine and mouse immunoglobulins. The molecules may encompass chimera made from canine IgG constant heavy and light domains and murine immunoglobulin heavy and light variable region domains that have an affinity for exon 3 of canine IgE.

The terms anti-canine IgE mAb, chimeric mAb, recombinant mAb, and receptor as used herein encompass any and all conservative variants thereof and are considered to be within the scope of the present invention.

It is a feature of the present invention that administration of chimeric canine anti-IgE mAb or receptor is useful in the method of treatment of canine allergies. It is also a feature of the invention that administration of compositions of the present invention lowers serum IgE levels in canines.

The chimeric canine anti-IgE mabs and receptors of the present invention are capable of disrupting or blocking the interaction between IgE and its receptors. Generally, the interference between IgE and its receptors is independent of the type of allergen causing or likely to cause allergic symptoms.

In embodiments of the present invention, chimeric canine anti-IgE mAbs and receptors of the present invention may act by blocking the binding of IgE to its receptors on mast cells or basophils by blocking the binding site on IgE molecules or otherwise interfering with the binding of IgE to its receptor. The chimeric canine anti-IgE mAbs and receptors of the present invention may also act by binding soluble IgE in plasma which complex is then removed from circulation by the body's normal mechanisms. In other embodiments of the present invention, the chimeric canine anti-IgE mabs or receptors may act by binding IgE on B-cells and eliminating clonal populations of IgE+ B-cells. The chimeric canine anti-IgE mAbs or receptors of the present invention may also act by inhibiting IgE production. While not wanting to be bound by any particular theory, it is believed that the mAb or receptor may bind to B cells and induce a cross-linking event which may induce apoptosis of cells or lead to inhibitory signals which down-regulate or eliminate IgE synthesis. Additionally, the binding of serum IgE, free IgE that is, may allow another regulatory molecule which may normally bind serum IgE in the exon 3 region to bind to IgE on the B cell and effect, subsequently, IgE synthesis through negative signals associated with and resulting from such binding.

In another embodiment, the chimeric canine anti-IgE mabs or receptors of the present invention may comprise or be formulated with IgG heavy chain sequences to enhance the half-life of the molecules in vivo or increase their activity.

The method of treating dogs suffering allergic symptoms or of preventing allergic symptoms in dogs generally may comprise the administration of a therapeutic amount of a chimeric canine anti-IgE mAb or receptor to the treated animal. Precise dosages of chimeric canine anti-IgE mAb or receptor and administration parameters will be established in a manner consistent with that known to those of ordinary skill in the art. This may involve taking into account one or more of the following factors, although this list is intended to be representative and is not intended to be exclusive of other parameters which may be known or become known to those of ordinary skill in the art: the presence and severity of allergic symptoms, the species of dog, the condition of the individual patient, the site of delivery, the method and length of administration, and other factors known to those of ordinary skill in the art or which may become known in the future.

Similarly, the dose of the chimeric canine anti-IgE mAb or receptor administered may be dependent on consideration of the properties of the IgE heavy chain isotypes used and other factors. For example, these considerations may include the binding activity and in vivo plasma half-life, the concentration of the chimeric canine anti-IgE mAb or receptor in the formulation, the administration route, the site and rate of dosage, and the clinical tolerance of the patient involved. This list is not intended to be limiting. and the person of ordinary skill in the art will realize that other factors may also be relevant and advantageous to consider.

The therapeutic amount of the instant chimeric canine anti-IgE mAb or receptor may be administered in dosages and for a period of time sufficient to alleviate or suppress allergic symptoms and/or to decrease serum IgE levels and/or suppress IgE production or activity.

In general, the formulations of the present invention may contain other components in amounts that do not interfere with the preparation of stable and efficacious forms of the canine anti-IgE mAb or receptor. Any additional components administered with the chimeric canine anti-IgE mAb or receptor may be present in amounts suitable for effective, safe pharmaceutical administration. Pharmaceutical excipients known to those of ordinary skill in the art may form a part of the subject compositions. For example, such excipients may include saline and other parenteral solutions, buffers and stabilizers, as well as any of the various suitable bulking agents, buffering agents, antioxidants, cosolvents and other ingredients known to those of ordinary skill in the art as being advantageous to include. In a preferred embodiment, the canine anti-IgE mAb or receptor may be formulated as a solution of protein in sterile PBS.

The chimeric canine anti-IgE mAb or receptor of the present invention may be administered in a way which is effective for disrupting, blocking or otherwise interfering with binding between IgE and its receptor or in a way which may enhance binding between the administered mAb or receptor and IgE. These methods will be apparent to those of ordinary skill in the art. In preferred embodiments, the chimeric canine anti-IgE mAb or receptor may be administered subcutaneously, intramuscularly or intravenously. Alternatively, the mAb or receptor may be formulated and administered via suspensions, tablets, capsules or suppositories for oral, rectal or vaginal administration.

The following examples further illustrate the cloning, expression, and purification of the 15A.2 mAb and are not intended to be limiting.

EXAMPLE I

Cloning of Mouse 15A.2 Variable Region

Mouse monoclonal 15A.2 variable region was cloned by RT-PCR from 15A.2 hybridoma cells. A commercially available kit (Novagen, Madison, Wis., Ig-Prime Kit) that consists of a set of degenerate PCR primers for the reverse transcription and amplification of IgVh and IgV1 mRNA's from mouse hybridoma cell lines was used as a source of primers to clone the 15A.2 mRNA's encoding the light and heavy variable domains. The 5' and 3' primers for the IgVh domain was MuIgVh5'-B and MuIgMvh3'-1 respectively. MuIgVh5'-B is a mixture of two primers in one tube (provided by Novagene), having the sequences GGGAAT-TCATGRAATGSASCTGGGTYWTYCTCTT (SEQ. ID NO:1) and ACTAGTCGACATGGACTCCAGGCT-CAATTTAGTTTTCCT (SEQ. ID NO:2). MuIgMvh3'-1 has the sequence CCCAAGCTTACGAGGGGGAAGA-CATTTGGGAA (SEQ ID NO: 3). The 5' and 3' primers for the IgV1 domain was MuIgλV15'-A and MuIgλV13'-1 respectively. The mRNA encoding the 15A.2 IgVh and IgV1 variable domains was reverse transcribed, amplified and cloned. MuIg(lambda)V15'-A has the sequence GGGAAT-TCATGGCCTGGAYTYCWCTYWTMYTCT (SEQ ID NO: 4). MuIg(lambda)V13'-1 has the sequence CCCAAGCTTAGCTCYTCWGWGGAIGGYGGRAA (SEQ ID NO:5).

The PCR reactions were performed as follows:

| Enzyme: | Taq polymerase | |
|---|---|---|
| 1) 94° C. | 20 seconds | 35 cycles |
| 60° C. | 58 seconds | |
| 72° C. | 20 seconds | |
| 2) 4° C. | Storage | |

Suitable clones of the 15A.2 IgVh and IgV1 variable domains were identified using restriction endonuclease analysis and DNA sequence analysis. Comparison of these DNA sequences to known mouse IgVh and IgV1 genes verified them as coding for the variable domains of a mouse monoclonal antibody.

EXAMPLE II

Cloning of Canine IgG Constant Region

The canine immunoglobulin light and heavy constant regions were cloned by RT-PCR from dog lymphocyte cells. PCR primers based on the sequence of the constant domain of canine IgG was used for the reverse transcription and PCR amplification of mRNA encoding the immunoglobulin constant domains (disclosed in U.S. Pat. No. 5,593,861 to Maeda et al.). The PCR reaction was the same as listed above. PCR products were cloned and subjected to DNA sequence analysis. Suitable clones of the immunoglobulin constant domains were identified using restriction endonuclease analysis and DNA sequence analysis. Comparison of these DNA sequences to known immunoglobulin genes verified them as coding for the constant domains of a canine immunoglobulin.

EXAMPLE III

Cloning of Full Length Mouse/Canine Chimeric 15A.2

The conventional process for the preparation of chimeric monoclonal antibodies was used to construct a full length mouse/canine chimeric 15A.2 monoclonal antibody genes. The mouse 15A.2 variable region encoding sequence and the appropriate canine constant region coding sequence were linked together via PCR and cloned. After verification of the chimeric genes by DNA sequence analysis, a suitable mouse/canine chimeric 15A.2 light chain gene and mouse/canine 15A.2 heavy chain gene was selected for expression and protein production of the chimeric protein.

Identification of Functional Clones

Functional clones of the 15A.2 chimeric heavy and light chains were identified using a COS cell transient expression system. The full-length heavy chain and the full-length light chain were cloned downstream in correct orientation of the CMV promoter on the pcDNA3.1 vector (Invitrogen, Carlsbad, Calif.). The immunoglobulin leader signals on the proteins would cause the proteins to be secreted out of the cell into culture supernatant. Co-transfection of both DNAs into COS cells allowed transient gene expression, protein production and assembly of functional chimeric antibodies in the cell. IgE binding ELISA and anti-canine IgG ELISA were used to detect functional antibody activity in cell culture supernatants. The clones which gave the best binding activity were used to construct vectors for chimeric monoclonal antibody production in a baculovirus expression system. The sequences of both heavy chain and light chain are shown as follows:

Chimeric 15A.2 heavy chain DNA sequence (SEQ. ID NO. 6)

ATGAAATG-
GAGCTGGGTTTTTCTCTTTCTCCTGT-
CACTAACTGCGGGTGTGTTCT CTGAGGTTCAGCT-
GCAGCAGTCTGGACCTGAGCTGGTGAAGCCTGGG
GCTTCAGTGAAGA TATCCTGCAAGGCTTCTGGT-
TACTCATTTACTGACTACTTTAT-
GAACTGGGTGATGCAGA GCCATGGAAAGAGCCT-
TGAGTGGATTGGTCGTATTAATCCTTTCAATGGTGA
TCCTTTCT ACAACCAGAAGTTCAAGGGCAAGGC-
CACATTGACTGTAGACAAATCCTCTAGCACAGCCC
ACATGGAGCTCCGGAGCCTGGCATCT-
GAGGACTCTGCAGTCTATTATTGTGCAAGATTCT
ACTACGGACGTTACTATGCTATGGAC-
TACTGGGGTCAAGGAACCTCAGTCACCGTCTCCT
CAGCCTCCACCACGGCCCCTCG-
GTTTTCCCACTGGACCCAGCT-
GCGGGTCCACTTCCG GCTCCACGGTGGCCCTGGC-
CTGCCTGGTGTCAGGCTACTTCCCCGAGCCTGTA
ACTGTGT CCTGGAATTCCGGCTCCTTGACCAGCG-
GTGTGCACACCTTCCCGTCCGACCTGCAGTCCT
CAGGGCTCTACTCCCTCAGCAGCATGGT-
GACAGTGCCCTCCAGCAGGTGGTCCAGCGAGA
CCTTCACCTGCAACGTGGCCCACCCGGC-
CAGCAAAACTAAAGTAGACAAGCCAGTGCCCA
AAAGAGAAAATGGAAGAGTTCCTCGC-
CCACCTGATTGTCCCAAATGCCCAGCCCCTGAAA
TGCTGGGAGGGCCTTCGGTCT-
TCATCTTTCCCCCGAAACCCAAGGACAC-
CCTCTTGATTG CCCGAACACCTGAGGTCACATGT-
GTGGTGGTGGATCTGGGACCAGAAGACCCTGAGG
TGC AGATCAGCTGGTTCGTGGACGGTAAGCA-
GATGCAAACAGCCAAGACTCAGCCTCGTGAGG
AGCAGTTCAATGGCACCTACCGTGTGGT-
CAGTGTCCTCCCCATTGGGCACCAGGACTGGC
TCAAGGGGAAGCAGTTCACGTGCAAAGT-
CAACAACAAAGCCCTCCCATCCCCGATCGAGA
GGACCATCTCCAAGGCCAGAGGGCAGGC-
CCATCAGCCCAGTGTGTATQTCCTGCCGCCAT
CCCGGGAGGAGTTGAGCAAGAACACAGT-
CAGCTTGACATGCCTGATCAAAGACTTCTTCC CAC-
CTGACATTGATGTGGAGTGGCAGAG-
CAATGGACAGCAGGAGCCTGAGAGCAAGTACC
GCACGACCCCGCCCAGCTGGACGAG-
GACGGGTCCTACTTCCTGTACAGCAAGCTCTCTG
TGGACAAGAGCCGCTGGCAGCGGGGAGA-
CACCTTCATATGTGCGGTGATGCATGAAGCTC
TACACAACCACTACACACAGAAATC-
CCTCTCCCATTCTCCGGGTAAATGA

Chimeric 15A.2 light chain DNA sequence (SEQ. ID NO. 7)

ATGGCCTGGATTTCACTCTTAT-
TCTCTCTCCTGGCTCTCAGCTCAGGGGCCATTT
CCCAGGCTGTTGTGACTCAGGAATCTG-
CACTCACCACATCACCTGGTGAAACAGTCACAC
TCACTTGTCGCTCAAGTACTGGGGCTGT-
TACAACTAGTAACTATGCCAACTGGGTCCAAG
AAAAACCAGATCATTTATTCACTG-
GTCTAATAGGTGGTCCCAACAAC-
CGAGCTCCAGGTG TTCCTGCCAGATTCTCAG-
GCTCCCTGATTGGAGACAAGGCTGCCCTCACCAT
CACAGGGG CACAGACTGAGGATGAG-
GCAATATATTTCTGTGCTCTATGGTA-
CAGCAACCATTGGGTGT TCGGTGGAGGAAC-
CAAACTGACTGTCCTAGGCCAGCCCAAGGCCTCC
CCCTCGGTCACAC TCTTCCCGCCCTCCTCTGAG-
GAGCTCGGCGCCAACAAGGCCACCCTG-
GTGTGCCTCATCA GCGACTTCTACCCCAGCGGCGT-
GACGGTGGCCTGGAAGGCAAGCGGCAGCCCCGT
CACCC AGGGCGTGGAGACCACCAAGCCCTC-
CAAGCAGAGCAACAACAAGTACGCGGC-
CAGCAGCT ACCTGAGCCTGACGCCTGACAAGTG-
GAAATCTCACAGCAGCTTCAGCTGCCTGGTCACGC
ACGAGGGGAGCACCGTGGAGAAGAAG-
GTGGCCCCCGCAGAGTGCTCTTAG

EXAMPLE IV

Expression of Chimeric 15A.2 in Insect Cells

A baculovirus expression system was used for larger scale production of the chimeric 15A.2mouse/canine monoclonal antibody. Baculovirus expression is a common technique and the methods are well known to one of ordinary skill in the art. The 15A.2 heavy chain DNA was cloned into PharMingen's (San Diego, Calif.) pAc LIC baculovirus transfer vector for recombination into baculovirus. Chimeric 15A.2 light chain DNA was cloned into PharMingen's pAcHis NT-A™ baculovirus transfer vector for recombination into baculovirus. Recombination and amplification of both virus constructs were amplified in insect sf-9 cells. The chimeric 15A.2 was expressed using insect High Five cells. The infection conditions were as following:

High Five cell density for infection: $1.5\times10^6$/ml

MOI for heavy chain virus infection: 10

MOI for light chain virus infection: 3

Time of protein expression: 72 hours 15A.2 was expressed and secreted into the cell culture media.

Purification of Chimeric 15A.2 Protein

Figures 1, 2A:
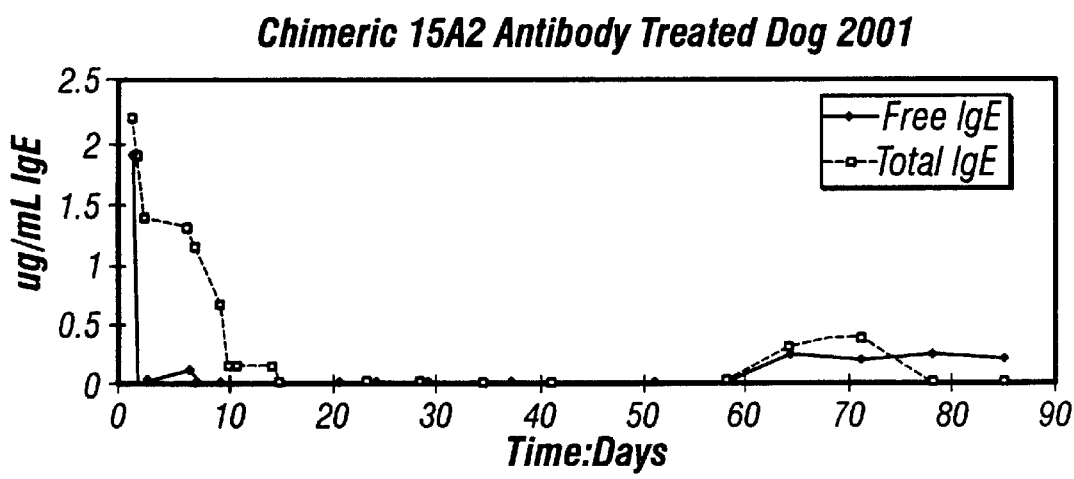
Figures 2, 2A:
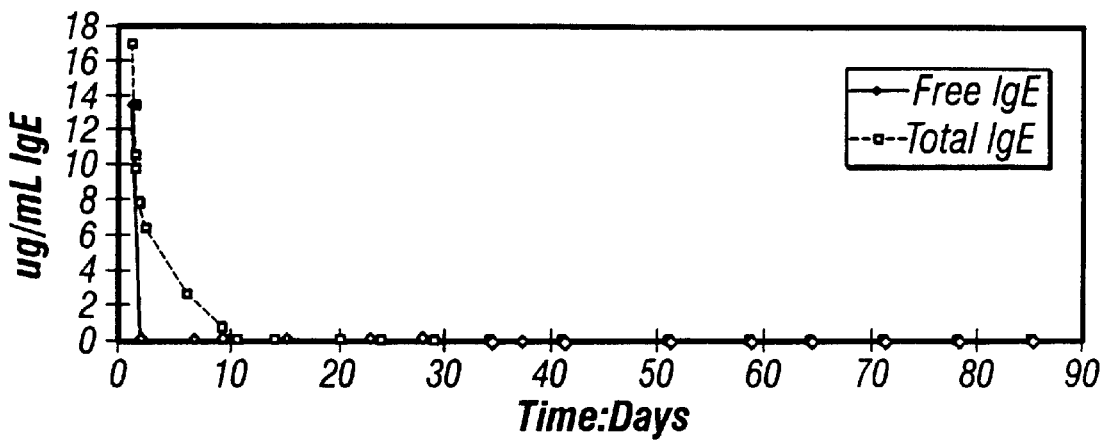
FIGS. 2(a & b) depict time course data for (free and total IgE) circulating IgE levels in 2 control and 3 experimental dogs following administrations of a recombinant chimeric anti-IgE mAb designated c15A.2. The mAb 15A.2 and its specificity is disclosed in the pending patent application Ser. No. 09/281,760, filed on Mar. 30, 1999.
Figures 2, 2A, 3:
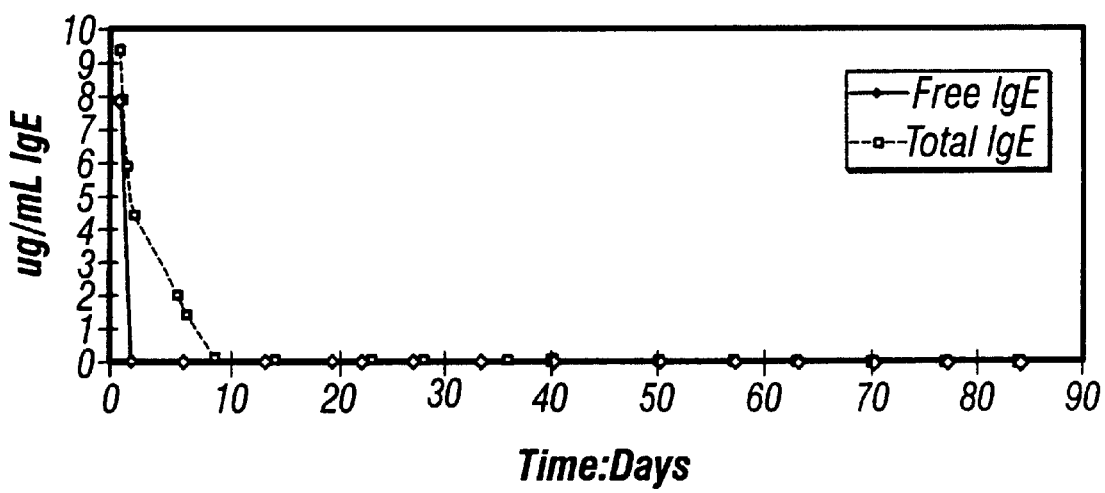
FIG. 3 depicts time course data for c15A.2 activity in dogs following a course of administration of chimeric antibody.
Figures 1, 2B:
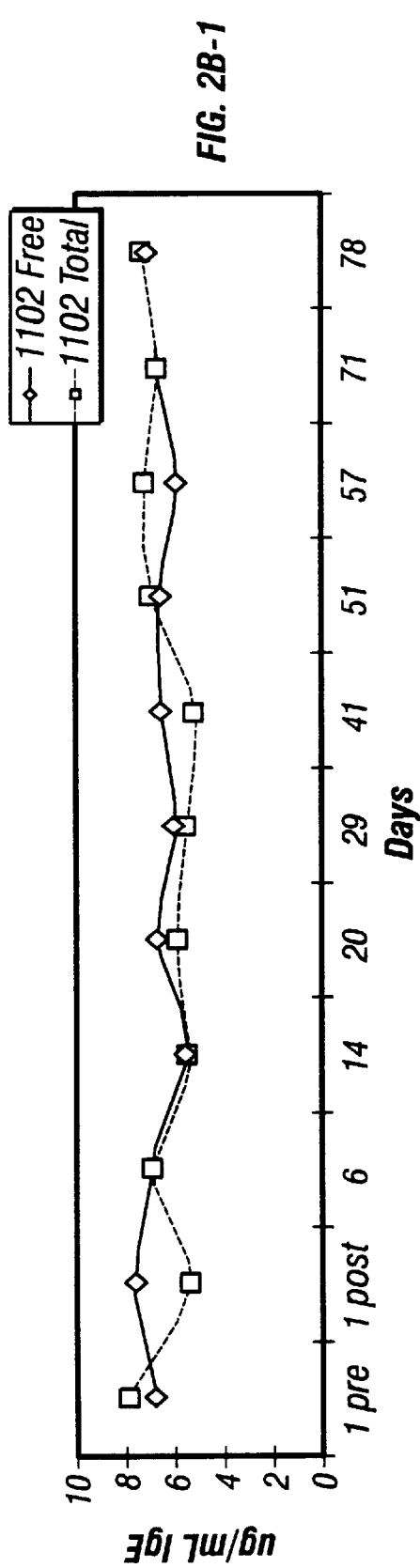
Figures 2, 2B:
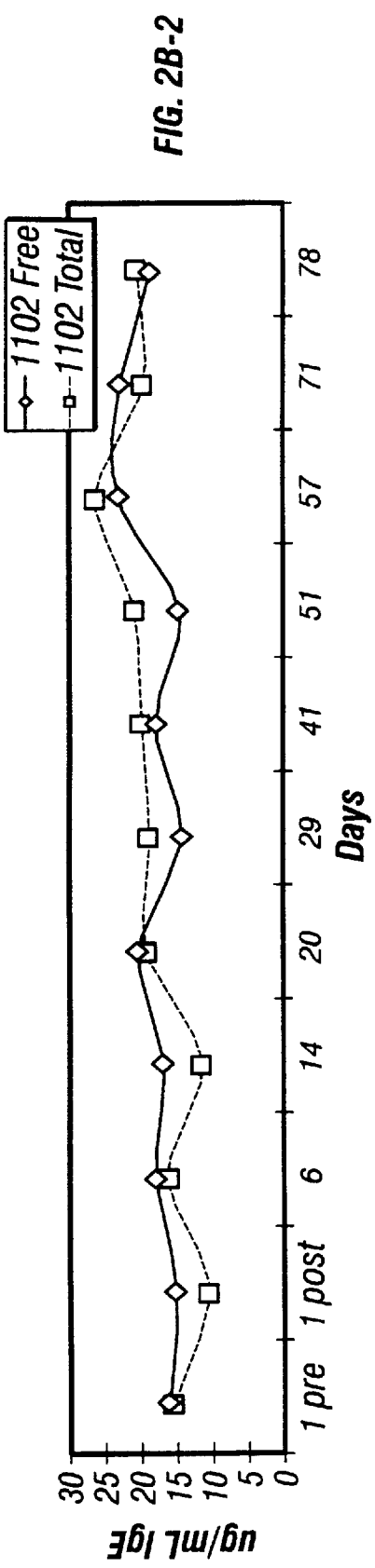
Figure 3:
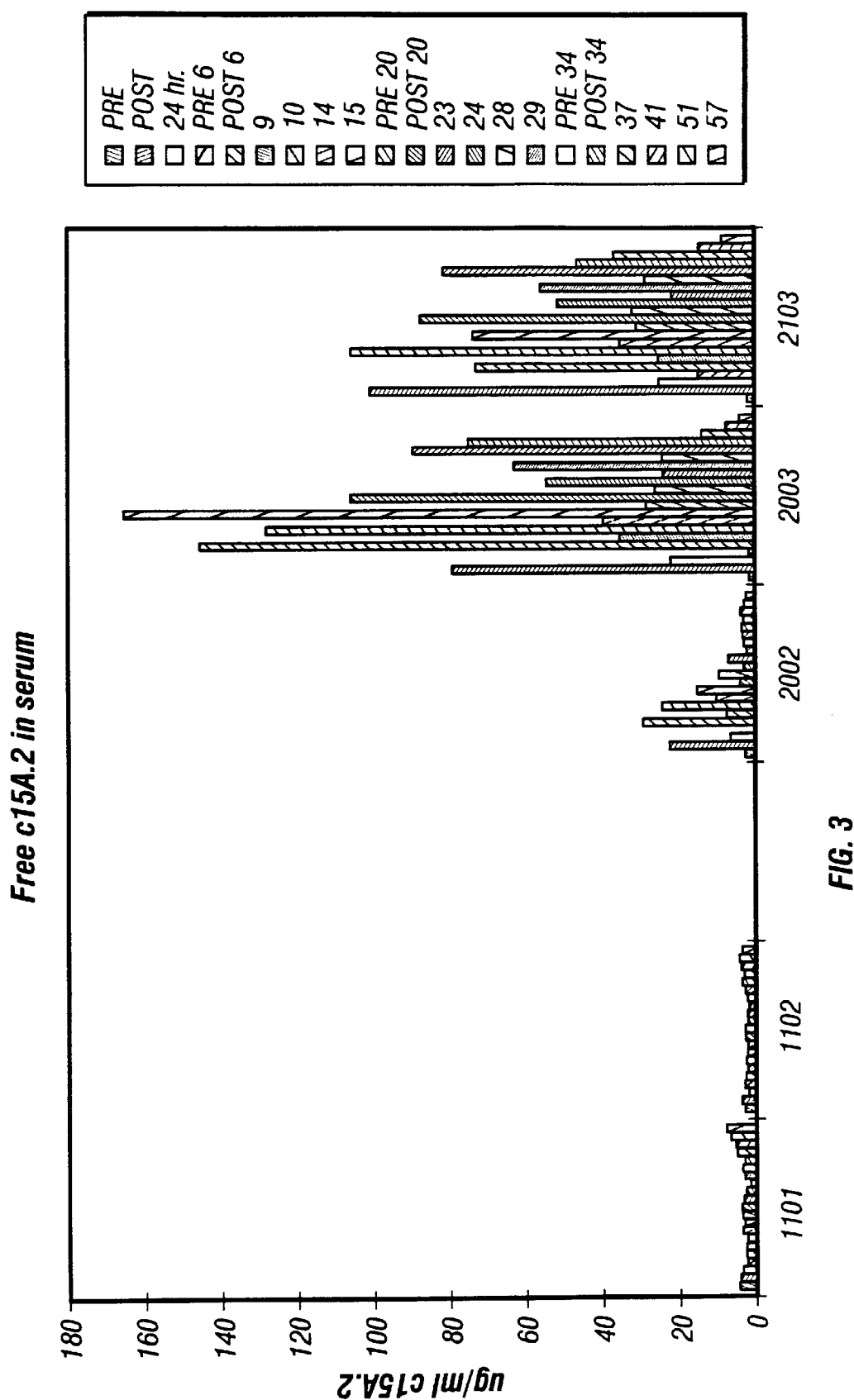
Figure 4:
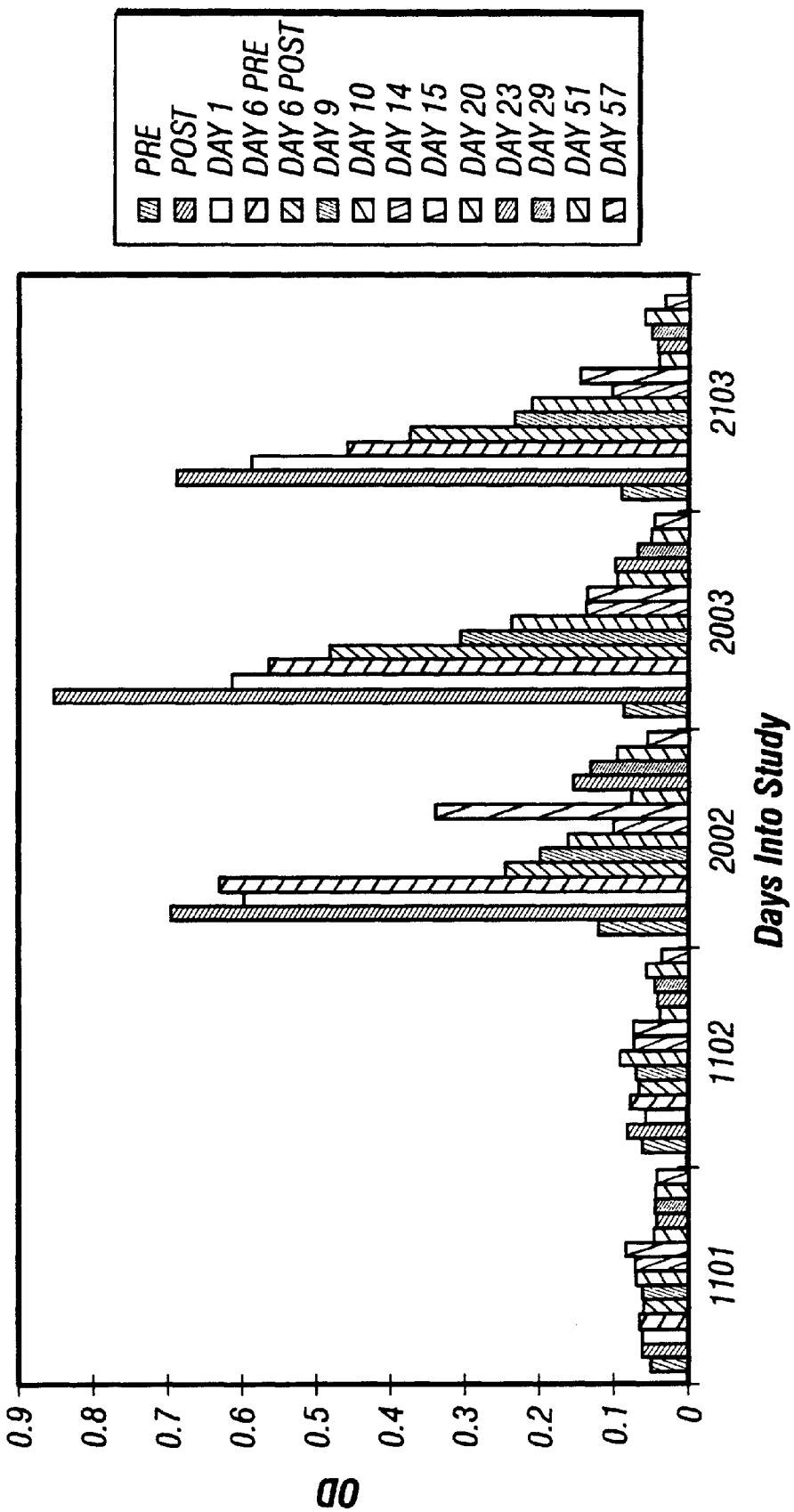
FIG. 4 depicts time course data for circulating IgE complexed with c15A.2 in 3 dogs following administration of 8 courses of chimeric antibody.
Figure 5:
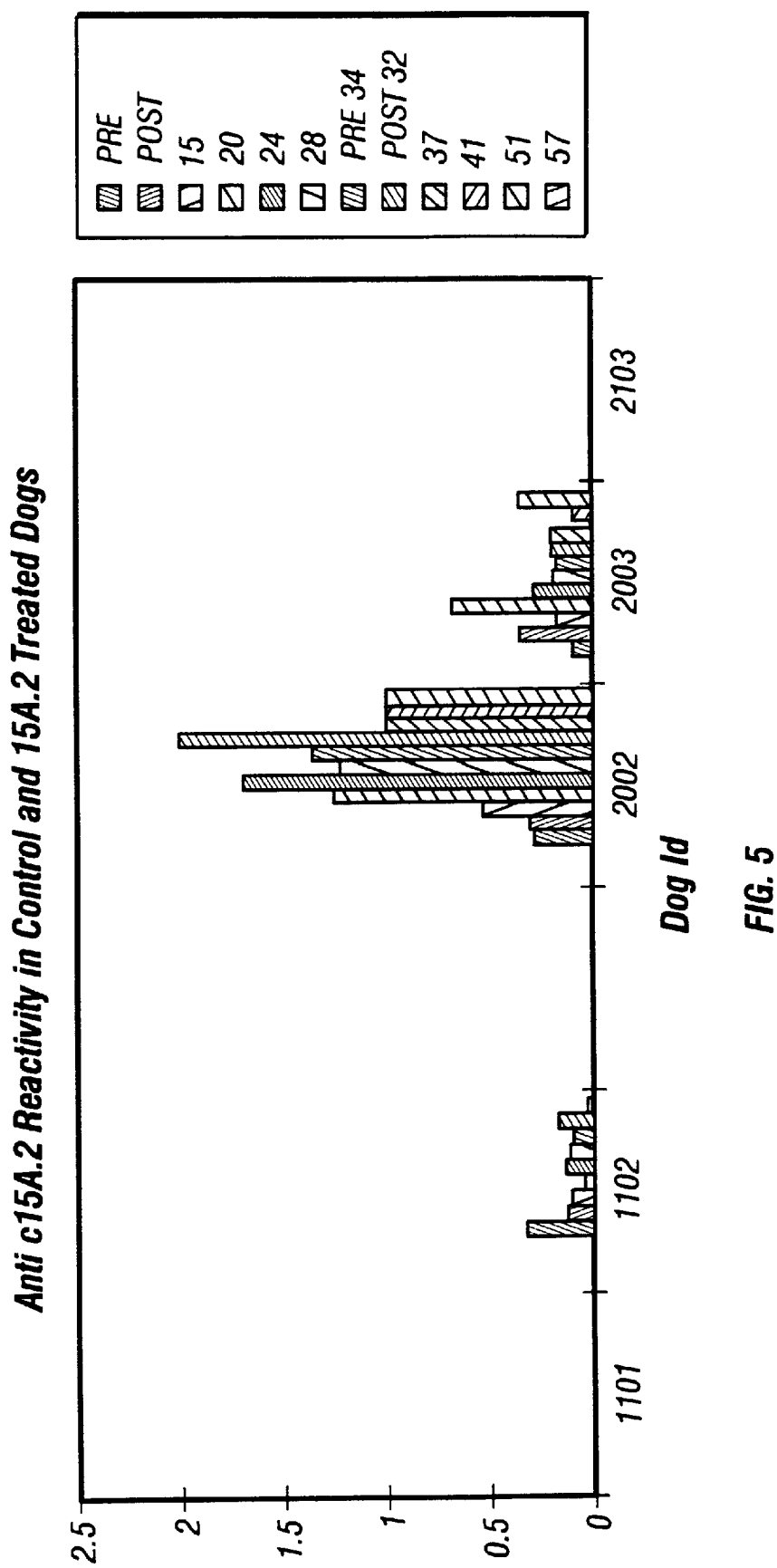
FIG. 5 depicts time course data for anti-chimeric 15A.2 activity observed in the serum of the experimental dogs over the course of administration of the chimeric antibody.

The general purification scheme is as following:

1. Cell clarification:

The cell culture supernatant containing 15A.2 protein was harvested 72 hours after infection. The supernatant was filtered through Millipore's (Bedford, Mass.) MILLIGUARD™ cartridge filtration system for cell clarification. Other filtration systems which have a pore size of 0.2 μm and are high capacity filters with low protein binding, and are able to withstand high pressure will also be suitable. The clarified supernatant was then concentrated for column chromatography.

2. Protein A Column Chromatography:

The concentrated sample was loaded onto a protein A column equilibrated with PBS buffer. The 15A.2 protein was eluted by pH gradient generated by mixing 4% glycerol, PBS, pH 7.2 and 4% glycerol, 25 mM sodium citrate buffer, pH 2.5. The protein was eluted at about pH 4.

3. Ion-exchange Column Chromatography:

The protein A purified 15A.2 was loaded onto the Q Sepharose™ (Pharmacia, Uppsala, Sweden) column equilibrated with 4% glycerol, PBS, pH 7.2 to remove contaminated proteins, DNA, RNA, virus, etc. Similar ion exchange resin which remove DNA, RNA, endotoxin and other negatively charged materials from purified proteins may also be utilized. The flow-through was collected.

4. Sterilization:

The Q flow-through 15A.2 was concentrated and sterilized by filtering through 0.2. μm filter unit. The final buffer component is as following:

0.7×PBS 6.5 mM sodium citrate

4% glycerol pH: ~7.0

The protein has at least 95% purity as indicated by SDS-PAGE protein gel and stored at −80° C. for future use.

EXAMPLE V

Recombinant Canine Anti-IgE MAb, (c15A.2): Effects on IgE Activity in Vitro and in Vivo Purified c15A.2 as obtained from Example IV was tested for its ability to prevent the binding of canine IgE to the canine IgE receptor in vitro (FIG. 1). The amount of c15A.2 required to neutralize IgE in the sera of three dogs. designated 2002, 2003 and 2103 was determined by the serum neutralization assay and is shown in FIG. 8. The time course and events for the 40 day experimental period are summarized in FIGS. 2*a* and 2*b*. Dogs were sensitized to ragweed at birth at Lovelace-Respiratory Research Institute (Albuquerque, N.Mex.) and used in studies to test the efficacy assessed by the dogs' ability to develop a subcutaneous skin response following administration of allergen.

The c15A.2 was administered to dogs 2002, 2003 and 2103 every five days for eight consecutive treatments. The amount of administered c15A.2 in the first treatment was equivalent to 10× the concentration of measurable free serum IgE concentration three days prior to the start of administration. Doses 1 and 2 received 10×free serum IgE concentration. All subsequent dosages were set at 5×free serum IgE concentration. The test article was diluted into sterile PBS at the concentration required to deliver 10× or 5×serum IgE concentration by intravenous infusion over a 30 minute period.

FIG. 2*a* follows the level of free and total serum IgE in each dog versus time, based upon dosages of c15A.2 mAb administered. Additional c15A.2 was then administered every five days for a total of 40 consecutive days. Serum IgE levels are assayed by standard ELISA techniques that are well known to those of ordinary skill in the art. IgE levels are generally considered to be undetectable in the ELISA technique below about 1 ng/ml.

FIG. 2*a* also shows that free IgE in the experimental dogs dropped to undetectable levels within 60 minutes and did not return during the entire 40 day-treatment period. The levels of free serum IgE in control dogs 1101 and 1102 receiving only saline, did not change significantly during this period (FIG. 2*b*). The assay used in these experiments consisted of an ELISA solid phase capture with mouse 15A.2 antibody and detection with another HRPO-conjugated mAb, 14K.2 which recognizes exon 4 of canine IgE. The assay detects all serum IgE not bound by c15A.2.

Total IgE bound by c15A.2 dropped more slowly than free IgE in experimental dogs presumably because it recirculated and was eventually cleared from circulation. The assay used here consisted of an ELISA capture with mAb 14K.2 and detection with another anti-canine IgE mAb, which is not inhibited from binding by c15A.2. In dogs 2003 and 2103 free and total serum IgE has remained undetectable in assays for greater than 60 days following the last dose of administration of recombinant antibody. In dog 2002, 30 days after administration of chimeric antibody was halted, free serum IgE was detectable at about 200 ng/ml and remained at this level for the remaining 30 days of observation.

These data show the effects of a recombinant antibody of the present invention in: (1) clearing the serum of circulating IgE; and (2) providing a method for affecting the process by which IgE is replenished. These results are surprising given that serum IgE is understood to have a short half-life, probably on the order of about two days, and that recombinant or chimeric molecules may likewise exhibit relatively short half-lives in vivo. In untreated animals, circulating serum IgE is believed to be entirely replenished every 4 to 5 days, yet following administration of a canine anti-IgE mAb 15A.2 of the present invention, serum IgE levels remained suppressed below the level of detection 18 days after administration of the chimeric antibody.

EXAMPLE VI

Clearance of the c15A.2

The presence of free chimeric 15A.2 in the serum of dogs 2002, 2003 and 2103, was determined by ELISA using a recombinant canine IgE solid phase with detection by a polyclonal goat anti-canine IgG conjugate. FIG. 3 shows that the levels of c15A.2 in serum rise and fall consistently with the beginning and ending of each 5-day administration period. Free c15A.2 is still detectable (X μg/ml) in the serum of experimental dogs 24 days post-infusion.

Immune complexes of c15A.2 and canine IgE were measured by ELISA on a 14K.2 solid phase and detected by polyclonal anti-dog IgGfc conjugate. These data, summarized in FIG. 4, show that complexed IgE is detected at high concentration early in the time course of treatment, but the level of complexes consistently falls over time. By day 28 no immune complexes are detected in dogs receiving c15A.2. This result suggests that the complexes are cleared from the circulating pool of serum immunoglobulin and that synthesis of new IgE in this time frame is reduced or eliminated. No changes were observed in control dogs. No immune response to the chimeric monoclonal antibody c15A.2 was observed in dogs 2003 and 2103. At 28 days post primary infusion an immune response to the test article was observed in dog 2002. Data in FIG. 5 show that this response increases as more chimeric 15A.2 is administered and may play a role in the shorter serum half-life of c15A.2 in dog 2002 (FIG. 3).

EXAMPLE VII

Effect on Level of Expression of the High Affinity IgE Receptor on Basophils upon Administration of Canine Anti-IgE mAb 15A.2 (c15A.2)

At five days, 14 days, and 29 days following the start of the c15A.2 administration 10 ml of whole blood was removed. Semi-purified populations of peripheral blood leukocytes were prepared by density gradient centrification and stained with reagents for two-dimensional flow cytometric analyses. The reagents used in these experiments were FITC-conjugated, anti-canine high-affinity IgE receptor mAb 9L.4 and PE-conjugated 14K.2. The cells double staining for these antibodies and resident in quadrant four (upper right quadrant) of the dot blot diagrams in FIG. 6 are basophils.

Figure 6:
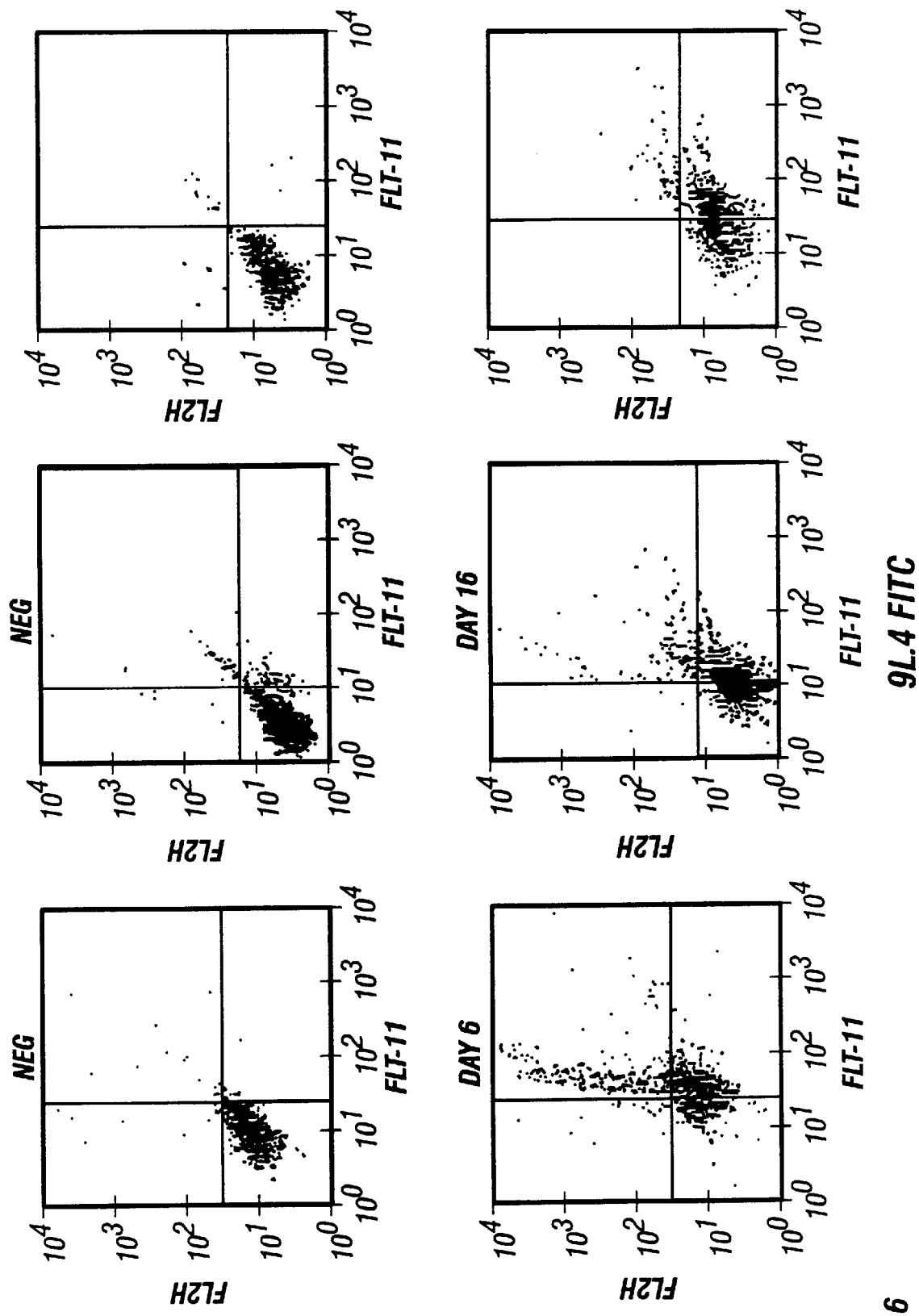
FIG. 6 depicts flow cytometric data from a dog, double-stained with PE-labeled anti-exon 4 canine IgG mAb 14K.2 and FITC-labeled anti-canine IgE receptor mAb 9L.4.four days following a first course, three days following a second course and 5 days following a $5^{th}$ course of administration of chimeric anti-15A.2 mAb.

Data in FIG. 6 are for dog 2002 and are representative. The number of double staining cells in quadrant decreases over the time course of administration of c15A.2. The data suggest that the level of expression of high affinity IgE receptors in basophils is reduced by over 90% after 29 days of administration of c15A.2 to the experimental dog 2002. Elimination of serum IgE over time leads to a reduction in expression of receptors for IgE on basophils and may reflect a similar response in skin mast cells. A reduced mast cell expression of high affinity IgE receptors will lead to a reduction or elimination of skin test reactivity to allergen.

EXAMPLE VIII

Effect on Ragweed Skin Test Reactivity of Administration of Canine Anti-IgE mAb 15A.2

Figure 7A:
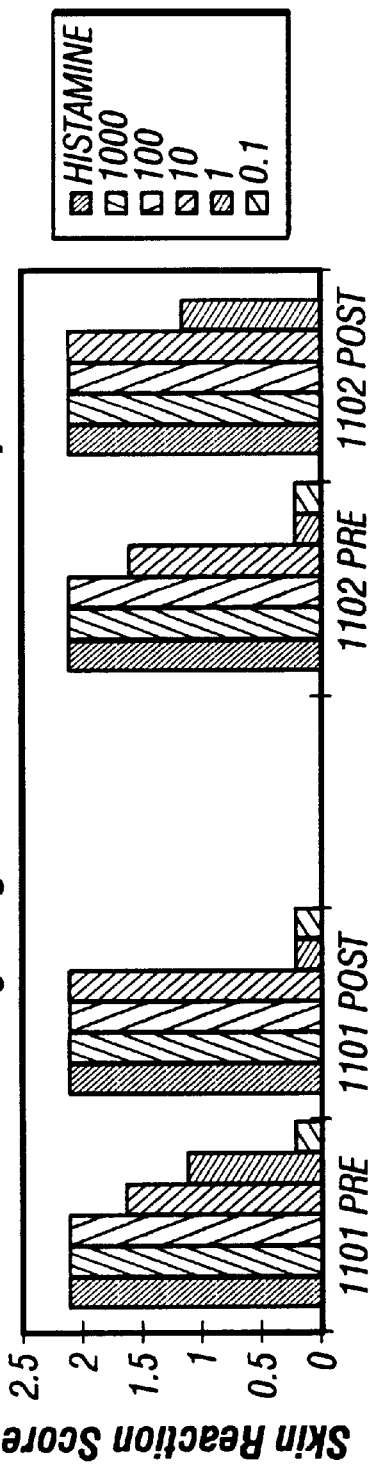
FIG. 7 depicts time course data for Ragweed skin test reactivity in dogs prior to, and 3 days and 7 days following eight courses of administration of c15A.2 mAb.
Figure 7B:
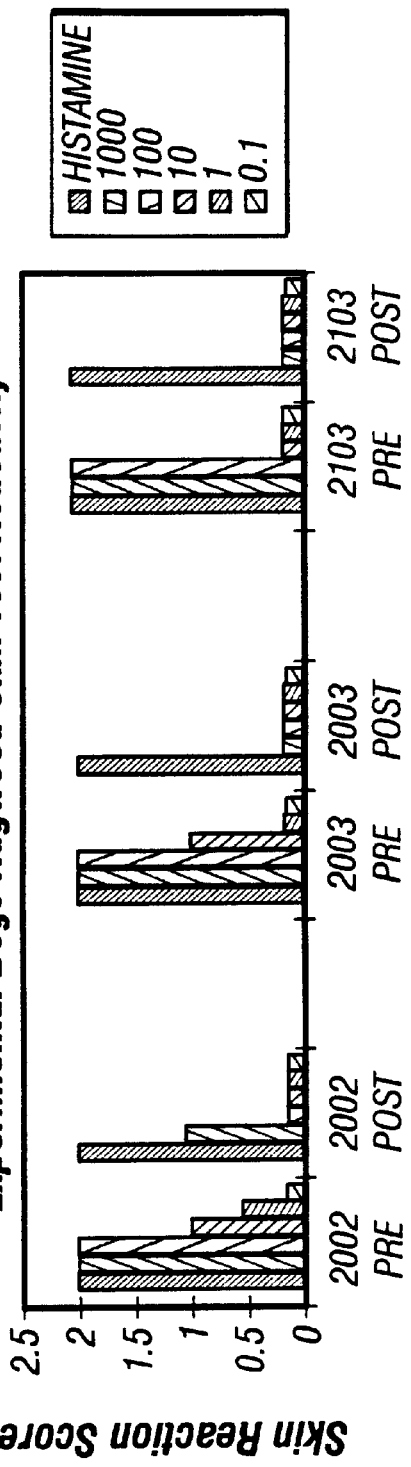
Figures 8, 9:
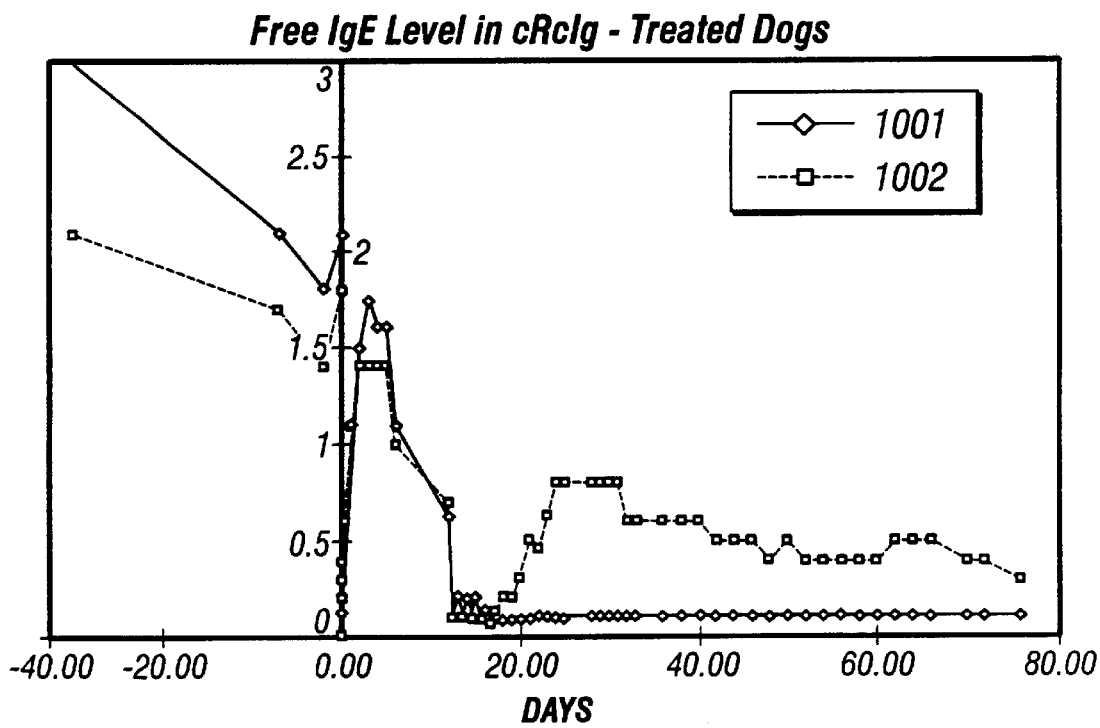
FIG. 8 depicts time: course data for circulating free IgE levels in dogs 1001 and 1002 following administrations of a recombinant receptor-IgG antagonist designated cRcIg.
FIG. 9 depicts free and total IgE in experimental dogs 1001 and 1002 over the time course of the experiment.

Ragweed sensitized dogs were infused with a 0.5% solution in PBS of Evans Blue Dye at 0.2 ml/kg and then challenged with. allergen 10 minutes later. Five, 10-fold serial dilutions of ragweed allergen in PBS starting at 1000 PMU/ml were prepared and 100 µl injected subcutaneously in a shaved section of the torso. Saline (PBS) served as a negative control and histamine (100 µl of an 0.275 µg/ml dilution of histamine in PBS) served as a positive control. Reactivity was measured 10 minutes later as the swelling and blue-dye diffusion in the skin compared with the histamine control. A rating of two was given to an allergen dilution in which the reaction was equivalent in size and color to the histamine reaction. A rating of 1 was given for a reaction that was half of the histamine control and a rating of zero was given when the reaction was equivalent to the saline negative control. Three experimental, 2002, 2003 and 2103 and two control, 1101 and 1102, dogs were skin tested as described above 1 week prior to administration of c15A.2, and then at 3 days and 7 days following the last administration. FIG. 7 shows that in control dogs the skin response to ragweed allergen was similar throughout the study. In control dog, 1102 the ragweed skin response actually increased over time. In experimental dogs 2003 and 2103 the ragweed sensitivity after administration of c15A.2 for 40 days was completely absent for at least 7 days. Only dog 2002 showed any ragweed sensitivity at the highest ragweed concentration on day 3 post-infusion and that response was given a rating of 1 because of the spread of dye. It did not have the characteristic swelling seen in a 1 rating observed and recorded for the control dogs. At 7 days post-infusion for dog 2002 a response rating of 1 was given to the spots with 1000 PMU/ml, 100 PMU/ml and 10 PMU/ml. Again there was only color diffusion and no swelling. Given the fact that dog 2002 had no detectable free or total IgE during this skin-testing period, it seems likely that the skin reactions observed may not have been due to cross-linking of IgE on the mast cell high affinity IgE receptors. They may have been the result of some other skin reaction associated with the testing procedure.

EXAMPLE IX

Chimeric Canine Anti-IgE mAb Engineered for Long Serum Stability, Loss of Immunogenicity and for IgE+ B-cell Targeting The person of ordinary skill in the art will realize that one may also provide the canine anti-IgE mAb of the present invention in a form which comprises a greater portion of the molecule as Ig taken from the dog sequence, and therefore should be expected to have greater serum stability, loss of immunogenicity and more effectively target IgE+ B cells.

Therefore, in another example a chimeric canine anti-IgE mAb that is engineered for long serum stability and an inability to induce an immune response against it is administered to a dog. This mAb binds to IgE in serum and to IgE on the surface of IgE-producing B-cells but not to IgE on mast cells or basophils. IgE synthesis is consequently reduced or eliminated. The resulting reduced IgE levels cause reduction in mast cell IgE receptor expression and reduction in associated allergic reactivity.

EXAMPLE X

Recombinant Canine IgE Receptor Designated cRcIg —Cloning and Expression in Insect Cells The sequence that is believed to correspond to at least part of the α-subunit of the canine IgE receptor is set forth in the GENBANK database under Assession No. D16413.

The cRcIg receptor is comprised of the alpha domain of the receptor which binds IgE linked to exons 2 and 3 of canine IgE. The IgG heavy chain sections of the receptor are the same as exons 2 and 3 of the c15A.2.

DNA encoding the chimeric IgE receptor cRcIg was introduced into a baculovirus genome using standard procedures. High five insect cell cultures were infected with baculovirus producing cRcIg. The cRcIg protein was purified from the cell culture medium by chromatography on protein A, followed by removal of contaminating proteins by ion exchange chromatography. The DNA sequence of the recombinant IgE receptor cRcIg with corresponding translation is shown in FIG. 10.

The IgE receptor used in the study was a recombinant chimeric receptor-body, named cRcIg, composed of the soluble high affinity IgE receptor alpha unit fused with the canine IgG CH2 and CH3 domain. The soluble alpha subunit, which lacks the trans-membrane domain, was cloned by PCR using the information available in GeneBank. The IgG CH2 and CH3 domain was part of sequence of DE94 as claimed by the Chemo-Sero patent. The soluble receptor and DE94 CH2/CH3 were connected by PCR to form the full length cRcIg.

The full length cRcIg was cloned into PharMingen's baculovirus pHcHisTNA vector. The virus was amplified using sf-9 cells. The cRcIg protein was produced in a secreted form and expressed in High five cells for 48 hours with MOI (multiplicity of infection) at 5. The protein was purified based on the CH2/CH3 domain's binding to Protein A column. Detailed purification scheme is the same as that of 15A.2 as illustrated in Example IV.

The purified cRcIg was concentrated to 2.9 mg/ml, and sterilized by filtering through 0.2 μm filter unit. The final buffer component is as follows:

0.7×PBS 6.5 mM sodium citrate

15% glycerol pH: about 7.0

The protein has at least 95%.purity as indicated by SDS-PAGE protein gel and stored at −80° C. for future use.

EXAMPLE XI

Recombinant Canine IgE Receptor Effects on IgE Activity in Vitro and in Vivo Serum IgE level was determined by ELISA as described previously. Purified cRcIg as obtained from Example X was tested for its ability to prevent the binding of canine IgE to the canine IgE receptor in vitro. The amount of cRcIg required to neutralize serum IgE was measured by titration of purified cRcIg against dog sera in vitro. Purified cRcIg was then administered through I.V. injection as a bolus.

The recombinant canine IgE receptor cRcIg was therefore administered intravenously as a bolus to dogs 1001 and 1002. This amount of cRcIg was equivalent to 10× (141 mgs; 7.08 ml @ 2 mg/ml in dog 1002) or 20× (220 mgs; 11.04 ml @ 2 mgs/ml in dog 1001) the amount needed for 50% neutralization of recombinant receptor binding in vitro. Additional cRcIg was then administered at the dosage of 5 ml @ 2 mg/ml as a bolus to each dog for five consecutive days, on days 13–17. FIG. 9 follows the level of free serum IgE in each dog versus time. In both dogs, IgE returned rapidly to the circulation after the initial dose of cRcIg on Day 0. Serum IgE levels are generally assayed by standard ELISA techniques well known to those of ordinary skill in the art. IgE levels are generally considered to be undetectable in the ELISA technique below about 1 ng/ml.

In dog 1001, serum IgE was undetectable by assay for greater than two months following the last dose of recombinant IgE receptor. In dog 1002, serum IgE levels returned to detectable levels over a period of days following the final administration of the recombinant receptor. It is to be noted however, that although serum IgE levels increased in dog 1002 they did not return to the elevated levels which were present prior to the administration of the recombinant receptor on day 0. FIG. 10 shows total and free serum IgE levels in each of the dogs during the course of the experiment. These data show that circulating IgE was not immediately removed from serum. Free serum IgE is unavailable but total IgE, presumably that complexed with cRcIg, was still in circulation.

These data document the effects of a recombinant receptor of the present invention in: (1) clearing the serum of circulating IgE; and (2) providing a method for affecting the process by which IgE is replenished.

EXAMPLE XII

Peptides Which Bind to Canine IgE and Prevent Binding to the IgE Receptor and/or Bind to IgE on B cells and Affect Synthesis of IgE The person of ordinary skill in the art will realize that peptides may be derived from combinatorial peptide libraries and comprise sequences of amino acids which when combined with IgE prevent binding to the IgE receptor. They are, then, peptides of any sequence of amino acids capable of binding to IgE, preferably exon 3 of IgE, and of preventing this IgE from binding to the IgE receptor. They may also bind to IgE on B cells.

Therefore, in another example peptides which bind to canine IgE are administered to a dog. The peptides bind IgE in serum and IgE on the surface of IgE-producing B-cells but not IgE on mast cells or basophils. IgE synthesis is reduced or eliminated. The resulting reduced IgE levels cause reduction in mast cell IgE receptor expression and reduction in associated allergic reactivity.

EXAMPLE XIV

Small Molecules Which Bind to Canine IgE and Prevent Binding to the IgE Receptor and/or Bind to IgE on B Cells and Affect Synthesis of IgE The person of ordinary skill in the art will realize that small organic molecules may be derived from combinatorial libraries and are screened in assays whereby the small organic molecules are isolated by their ability to inhibit IgE from binding to the IgE receptor. They, therefore may bind to IgE, preferably at a region within exon 3, and inhibit binding to the IgE receptor.

In another example a small molecule is administered to a dog. The small molecule binds IgE in serum and IgE on the surface of IgE-producing B-cells but not IgE on mast cells or basophils. IgE synthesis is consequently reduced or eliminated. The resulting reduced IgE levels cause reduction in mast cell IgE receptor expression and reduction in associated allergic reactivity.

CLOSING

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar to or equivalent to those described herein can be used in the practice or testing of the invention, the preferred methods and materials are described herein. All publications mentioned herein are fully incorporated herein by reference.

SEQUENCE LISTING

<160> NUMBER OF SEQ ID NOS: 10

<210> SEQ ID NO 1
<211> LENGTH: 34
<212> TYPE: DNA
<213> ORGANISM: Mus musculus

<400> SEQUENCE: 1
gggaattcat graatgsasc tgggtywtyc tctt                34

<210> SEQ ID NO 2
<211> LENGTH: 39
<212> TYPE: DNA
<213> ORGANISM: Mus musculus

<400> SEQUENCE: 2
actagtcgac atggactcca ggctcaattt agttttcct           39

<210> SEQ ID NO 3
<211> LENGTH: 32
<212> TYPE: DNA
<213> ORGANISM: Mus musculus

<400> SEQUENCE: 3
cccaagctta cgagggggaa gacatttggg aa                  32

<210> SEQ ID NO 4
<211> LENGTH: 33
<212> TYPE: DNA
<213> ORGANISM: Mus musculus

<400> SEQUENCE: 4
gggaattcat ggcctggayt ycwctywtmy tct                 33

<210> SEQ ID NO 5
<211> LENGTH: 32
<212> TYPE: DNA
<213> ORGANISM: Mus musculus
<220> FEATURE:
<221> NAME/KEY: misc_feature
<222> LOCATION: (24)..(24)
<223> OTHER INFORMATION: N stands for any nucleic acid

<400> SEQUENCE: 5
cccaagctta gctcytcwgw gganggyggr aa                  32

<210> SEQ ID NO 6
<211> LENGTH: 1425
<212> TYPE: DNA
<213> ORGANISM: Artificial Sequence
<220> FEATURE:
<223> OTHER INFORMATION: Mouse/canine chimeric 15A.2 heavy chain

<400> SEQUENCE: 6
atgaaatgga gctgggtttt tctctttctc ctgtcagtaa ctgcgggtgt gttctctgag      60
gttcagctgc agcagtctgg acctgagctg gtgaagcctg gggcttcagt gaagatatcc    120
tgcaaggctt ctggttactc atttactgac tactttatga ctgggtgat gcagagccat     180 ggaaagagcc ttgagtggat tggtcgtatt aatcctttca atggtgatcc tttctacaac    240
cagaagttca gggcaaggc cacattgact gtagacaaat cctctagcac agcccacatg    300
gagctccgga gcctggcatc tgaggactct gcagtctatt attgtgcaag attctactac    360

```
ggacgttact atgctatgga ctactggggt caaggaacct cagtcaccgt ctcctcagcc      420
tccaccacgg cccctcggt tttcccactg acccccagct gcgggtccac ttccggctcc       480
acggtggccc tggcctgcct ggtgtcaggc tacttccccg agcctgtaac tgtgtcctgg      540
aattccggct ccttgaccag cggtgtgcac accttcccgt ccgacctgca gtcctcaggg     600
ctctactccc tcagcagcat ggtgacagtg ccctccagca ggtggtccag cgagaccttc      660
acctgcaacg tggcccaccc ggccagcaaa actaaagtag acaagccagt gcccaaaaga     720
gaaaatggaa gagttcctcg cccacctgat tgtcccaaat gcccagcccc tgaaatgctg      780
ggagggcctt cggtcttcat ctttccccg aaacccaagg acaccctctt gattgcccga      840
acacctgagg tcacatgtgt ggtggtggat ctgggaccaa agaccctga ggtgcagatc       900 agctggttcg tggacggtaa gcagatgcaa acagccaaga ctcagcctcg tgaggagcag      960
ttcaatggca cctaccgtgt ggtcagtgtc ctccccattg gcaccagga ctggctcaag      1020 gggaagcagt tcacgtgcaa agtcaacaac aaagccctcc catccccgat cgagaggacc     1080
atctccaagg ccagagggca ggcccatcag cccagtgtgt atgtcctgcc gccatcccgg     1140
gaggagttga gcaagaacac agtcagcttg acatgcctga tcaaagactt cttcccacct    1200
gacattgatg tggagtggca gagcaatgga cagcaggagc tgagagcaa gtaccgcacg     1260 accccgcccc agctggacga ggacgggtcc tacttcctgt acagcaagct ctctgtggac     1320
aagagccgct ggcagcgggg agacaccttc atatgtgcgg tgatgcatga agctctacac     1380
aaccactaca cacagaaatc cctctcccat tctccgggta aatga                    1425

<210> SEQ ID NO 7
<211> LENGTH: 705
<212> TYPE: DNA
<213> ORGANISM: Artificial Sequence
<220> FEATURE:
<223> OTHER INFORMATION: Mouse/canine chimeric 15A.2 light chain

<400> SEQUENCE: 7
atggcctgga tttcactctt attctctctc ctggctctca gctcagggc catttcccag        60 gctgttgtga ctcaggaatc tgcactcacc acatcacctg gtgaaacagt cacactcact    120
tgtcgctcaa gtactgggc tgttacaact agtaactatg ccaactgggt ccaagaaaaa     180
ccagatcatt tattcactgg tctaataggt ggtcccaaca accgagctcc aggtgttcct    240
gccagattct caggctccct gattggagac aaggctgccc tcaccatcac aggggcacag    300
actgaggatg aggcaatata tttctgtgct ctatggtaca gcaaccattg ggtgttcggt     360
ggaggaacca aactgactgt cctaggccag cccaaggcct cccctcggt cacactcttc      420 ccgccctcct ctgaggagct cggcgccaac aaggccaccc tggtgtgcct catcagcgac     480
ttctacccca gcgcgtgac ggtggcctgg aaggcaagcg gcagcccgt cacccagggc      540 gtggagacca ccaagccctc caagcagagc aacaacaagt acgcggccag cagctacctg    600
agcctgacgc tgacaagtg gaaatctcac agcagcttca gctgcctggt cacgcacgag     660
gggagcaccg tggagaagaa ggtggccccc gcagagtgct cttag                    705

<210> SEQ ID NO 8
<211> LENGTH: 1300
<212> TYPE: DNA
<213> ORGANISM: Canis familiaris
<220> FEATURE:
<221> NAME/KEY: CDS
<222> LOCATION: (8)..(1300)
```

<223> OTHER INFORMATION:

<400> SEQUENCE: 8

```
ccgcgag atg cct gct tcc atg gga ggc cct gcc ctg ctg tgg cta gcg       49
        Met Pro Ala Ser Met Gly Gly Pro Ala Leu Leu Trp Leu Ala
        1               5                  10 ctg ctg ctc tcc tct cca ggt gtc atg tca tca gat acc ttg aaa cct       97
Leu Leu Leu Ser Ser Pro Gly Val Met Ser Ser Asp Thr Leu Lys Pro
15                  20                  25                  30 aca gtg tcc atg aac ccg cca tgg aat aca ata ttg aag gat gac agt      145
Thr Val Ser Met Asn Pro Pro Trp Asn Thr Ile Leu Lys Asp Asp Ser
                35                  40                  45 gtg act ctt aca tgt act cgg aac aac tcc ctt gaa gtc gac tct gct      193
Val Thr Leu Thr Cys Thr Arg Asn Asn Ser Leu Glu Val Asp Ser Ala
            50                  55                  60 gtg tgg ctc cac aac aac act act tgg caa gag acc act tca cgt ttg      241
Val Trp Leu His Asn Asn Thr Thr Trp Gln Glu Thr Thr Ser Arg Leu
        65                  70                  75 gac atc aat aaa gcc caa atc cag gac agt ggg gag tac agg tgt cgg      289
Asp Ile Asn Lys Ala Gln Ile Gln Asp Ser Gly Glu Tyr Arg Cys Arg
    80                  85                  90 gaa aat aga tcc atc ctg agt gat cct gtg tac cta aca gtc ttc aca      337
Glu Asn Arg Ser Ile Leu Ser Asp Pro Val Tyr Leu Thr Val Phe Thr
95                  100                 105                 110 gag tgg ctg atc ctt caa gcc tct gcc aac gtg gtg atg gag ggt gag      385
Glu Trp Leu Ile Leu Gln Ala Ser Ala Asn Val Val Met Glu Gly Glu
                115                 120                 125 agc ttc ctc atc agg tgc cat agt tgg aag aat ttg agc ctc aca aag      433
Ser Phe Leu Ile Arg Cys His Ser Trp Lys Asn Leu Ser Leu Thr Lys
            130                 135                 140 gtg acc tac tac aag gat ggc atc ccc atc agg tac tgg tac gag aac      481
Val Thr Tyr Tyr Lys Asp Gly Ile Pro Ile Arg Tyr Trp Tyr Glu Asn
        145                 150                 155 ttc aac atc tcc att agc aac gtc aca acc aaa aac agc ggc aac tat      529
Phe Asn Ile Ser Ile Ser Asn Val Thr Thr Lys Asn Ser Gly Asn Tyr
    160                 165                 170 tcc tgc tca ggc cag atc cag cag aaa ggc tac acc tct aaa gtc ctc      577
Ser Cys Ser Gly Gln Ile Gln Gln Lys Gly Tyr Thr Ser Lys Val Leu
175                 180                 185                 190 aac att att gtg aaa aaa gag ccc acc aag caa aac aag tac tcc ggg      625
Asn Ile Ile Val Lys Lys Glu Pro Thr Lys Gln Asn Lys Tyr Ser Gly
                195                 200                 205 cta cac cgc cca cct gat tgt ccc aaa tgc cca gcc cct gaa atg ctg      673
Leu His Arg Pro Pro Asp Cys Pro Lys Cys Pro Ala Pro Glu Met Leu
            210                 215                 220 gga ggg cct tcg gtc ttc atc ttt ccc ccg aaa ccc aag gac acc ctc      721
Gly Gly Pro Ser Val Phe Ile Phe Pro Pro Lys Pro Lys Asp Thr Leu
        225                 230                 235 ttg att gcc cga aca cct gag gtc aca tgt gtg gtg gtg gat ctg gac      769
Leu Ile Ala Arg Thr Pro Glu Val Thr Cys Val Val Val Asp Leu Asp
    240                 245                 250 cca gaa gac cct gag gtg cag atc agc tgg ttc gtg gac ggt aag cag      817
Pro Glu Asp Pro Glu Val Gln Ile Ser Trp Phe Val Asp Gly Lys Gln
255                 260                 265                 270 atg caa aca gcc aag act cag cct cgt gag gag cag ttc aat ggc acc      865
Met Gln Thr Ala Lys Thr Gln Pro Arg Glu Glu Gln Phe Asn Gly Thr
                275                 280                 285 tac cgt gtg gtc agt gac ctc ccc att ggg cac cag gac tgg ctc aag      913
Tyr Arg Val Val Ser Asp Leu Pro Ile Gly His Gln Asp Trp Leu Lys
            290                 295                 300
```

```
ggg aag cag ttc acc tgc aaa gtc aac aac aaa gcc ctc cca tcc ccg       961
Gly Lys Gln Phe Thr Cys Lys Val Asn Asn Lys Ala Leu Pro Ser Pro
            305                 310                 315 atc gag agg acc atc tcc aag gcc aga ggg ctg gcc ata gcc agt gtg      1009
Ile Glu Arg Thr Ile Ser Lys Ala Arg Gly Leu Ala Ile Ala Ser Val
320                 325                 330 tat gtc ctg ccg cca tcc cgg gag gag ttg agc aag aac aca gtc agc      1057
Tyr Val Leu Pro Pro Ser Arg Glu Glu Leu Ser Lys Asn Thr Val Ser
335                 340                 345                 350 ttg aca tgc ctg atc aaa gac ttc ttc ccc cct gac att gat gtg gag      1105
Leu Thr Cys Leu Ile Lys Asp Phe Phe Pro Pro Asp Ile Asp Val Glu
            355                 360                 365 tgg cag agc aat gga cag cag gag cct gag agt aag tac cgc acg acc      1153
Trp Gln Ser Asn Gly Gln Gln Glu Pro Glu Ser Lys Tyr Arg Thr Thr
            370                 375                 380 ctg ccc cag ctg gac gag gac ggg tcc tac ttc ctg tac agc aag ctc      1201
Leu Pro Gln Leu Asp Glu Asp Gly Ser Tyr Phe Leu Tyr Ser Lys Leu
            385                 390                 395 tct gtg gat aag agc cgc tgg cag cgg gga gac acc ttc ata tgt gcg      1249
Ser Val Asp Lys Ser Arg Trp Gln Arg Gly Asp Thr Phe Ile Cys Ala
400                 405                 410 gtg atg cat gaa gct cta cac aac cac tac aca cag aaa tcc ctc tcc      1297
Val Met His Glu Ala Leu His Asn His Tyr Thr Gln Lys Ser Leu Ser
415                 420                 425                 430 cat                                                                  1300
His

<210> SEQ ID NO 9
<211> LENGTH: 431
<212> TYPE: PRT
<213> ORGANISM: Canis familiaris

<400> SEQUENCE: 9

Met Pro Ala Ser Met Gly Gly Pro Ala Leu Leu Trp Leu Ala Leu Leu
1               5                   10                  15

Leu Ser Ser Pro Gly Val Met Ser Ser Asp Thr Leu Lys Pro Thr Val
                20                  25                  30

Ser Met Asn Pro Pro Trp Asn Thr Ile Leu Lys Asp Asp Ser Val Thr
            35                  40                  45

Leu Thr Cys Thr Arg Asn Asn Ser Leu Glu Val Asp Ser Ala Val Trp
50                  55                  60

Leu His Asn Asn Thr Thr Trp Gln Glu Thr Thr Ser Arg Leu Asp Ile
65                  70                  75                  80

Asn Lys Ala Gln Ile Gln Asp Ser Gly Glu Tyr Arg Cys Arg Glu Asn
                85                  90                  95

Arg Ser Ile Leu Ser Asp Pro Val Tyr Leu Thr Val Phe Thr Glu Trp
            100                 105                 110

Leu Ile Leu Gln Ala Ser Ala Asn Val Val Met Glu Gly Glu Ser Phe
        115                 120                 125

Leu Ile Arg Cys His Ser Trp Lys Asn Leu Ser Leu Thr Lys Val Thr
130                 135                 140

Tyr Tyr Lys Asp Gly Ile Pro Ile Arg Tyr Trp Tyr Glu Asn Phe Asn
145                 150                 155                 160

Ile Ser Ile Ser Asn Val Thr Thr Lys Asn Ser Gly Asn Tyr Ser Cys
                165                 170                 175

Ser Gly Gln Ile Gln Gln Lys Gly Tyr Thr Ser Lys Val Leu Asn Ile
            180                 185                 190
```

-continued

```
Ile Val Lys Lys Glu Pro Thr Lys Gln Asn Lys Tyr Ser Gly Leu His
            195                 200                 205
Arg Pro Pro Asp Cys Pro Lys Cys Pro Ala Pro Glu Met Leu Gly Gly
    210                 215                 220
Pro Ser Val Phe Ile Phe Pro Lys Pro Lys Asp Thr Leu Leu Ile
225                 230                 235                 240
Ala Arg Thr Pro Glu Val Thr Cys Val Val Asp Leu Asp Pro Glu
                245                 250                 255
Asp Pro Glu Val Gln Ile Ser Trp Phe Val Asp Gly Lys Gln Met Gln
            260                 265                 270
Thr Ala Lys Thr Gln Pro Arg Glu Glu Gln Phe Asn Gly Thr Tyr Arg
        275                 280                 285
Val Val Ser Asp Leu Pro Ile Gly His Gln Asp Trp Leu Lys Gly Lys
    290                 295                 300
Gln Phe Thr Cys Lys Val Asn Asn Lys Ala Leu Pro Ser Pro Ile Glu
305                 310                 315                 320
Arg Thr Ile Ser Lys Ala Arg Gly Leu Ala Ile Ala Ser Val Tyr Val
                325                 330                 335
Leu Pro Pro Ser Arg Glu Glu Leu Ser Lys Asn Thr Val Ser Leu Thr
            340                 345                 350
Cys Leu Ile Lys Asp Phe Phe Pro Pro Asp Ile Asp Val Glu Trp Gln
        355                 360                 365
Ser Asn Gly Gln Gln Glu Pro Glu Ser Lys Tyr Arg Thr Thr Leu Pro
    370                 375                 380
Gln Leu Asp Glu Asp Gly Ser Tyr Phe Leu Tyr Ser Lys Leu Ser Val
385                 390                 395                 400
Asp Lys Ser Arg Trp Gln Arg Gly Asp Thr Phe Ile Cys Ala Val Met
                405                 410                 415
His Glu Ala Leu His Asn His Tyr Thr Gln Lys Ser Leu Ser His
            420                 425                 430

<210> SEQ ID NO 10
<211> LENGTH: 435
<212> TYPE: PRT
<213> ORGANISM: Canis familiaris

<400> SEQUENCE: 10

Met Pro Ala Ser Met Gly Gly Pro Ala Leu Leu Trp Leu Ala Leu Leu
1               5                   10                  15
Leu Ser Ser Pro Gly Val Met Ser Ser Asp Thr Leu Lys Pro Thr Val
            20                  25                  30
Ser Met Asn Pro Pro Trp Asn Thr Ile Leu Lys Asp Asp Ser Val Thr
        35                  40                  45
Leu Thr Cys Thr Arg Asn Asn Ser Leu Glu Val Asp Ser Ala Val Trp
    50                  55                  60
Leu His Asn Asn Thr Thr Trp Gln Glu Thr Thr Ser Arg Leu Asp Ile
65                  70                  75                  80
Asn Lys Ala Gln Ile Gln Asp Ser Gly Glu Tyr Arg Cys Arg Glu Asn
                85                  90                  95
Arg Ser Ile Leu Ser Asp Pro Val Tyr Leu Thr Val Phe Thr Glu Trp
            100                 105                 110
Leu Ile Leu Gln Ala Ser Ala Asn Val Val Met Glu Gly Glu Ser Phe
        115                 120                 125
Leu Ile Arg Cys His Ser Trp Lys Asn Leu Ser Leu Thr Lys Val Thr
```

-continued

```
            130                 135                 140
Tyr Tyr Lys Asp Gly Ile Pro Ile Arg Tyr Trp Tyr Glu Asn Phe Asn
145                 150                 155                 160

Ile Ser Ile Ser Asn Val Thr Thr Lys Asn Ser Gly Asn Tyr Ser Cys
                165                 170                 175

Ser Gly Gln Ile Gln Gln Lys Gly Tyr Thr Ser Lys Val Leu Asn Ile
                180                 185                 190

Ile Val Lys Lys Glu Pro Thr Lys Gln Asn Lys Tyr Ser Gly Leu His
                195                 200                 205

Arg Pro Pro Asp Cys Pro Lys Cys Pro Ala Pro Glu Met Leu Gly Gly
                210                 215                 220

Pro Ser Val Phe Ile Phe Pro Pro Lys Pro Lys Asp Thr Leu Leu Ile
225                 230                 235                 240

Ala Arg Thr Pro Glu Val Thr Cys Val Val Val Asp Leu Asp Pro Glu
                245                 250                 255

Asp Pro Glu Val Gln Ile Ser Trp Phe Val Asp Gly Lys Gln Met Gln
                260                 265                 270

Thr Ala Lys Thr Gln Pro Arg Glu Glu Gln Phe Asn Gly Thr Tyr Arg
                275                 280                 285

Val Val Ser Asp Leu Pro Ile Gly His Gln Asp Trp Leu Lys Gly Lys
                290                 295                 300

Gln Phe Thr Cys Lys Val Asn Asn Lys Ala Leu Pro Ser Pro Ile Glu
305                 310                 315                 320

Arg Thr Ile Ser Lys Ala Arg Gly Leu Ala Ile Ala Ser Val Tyr Val
                325                 330                 335

Leu Pro Pro Ser Arg Glu Glu Leu Ser Lys Asn Thr Val Ser Leu Thr
                340                 345                 350

Cys Leu Ile Lys Asp Phe Phe Pro Pro Asp Ile Asp Val Glu Trp Gln
                355                 360                 365

Ser Asn Gly Gln Gln Glu Pro Glu Ser Lys Tyr Arg Thr Thr Leu Pro
370                 375                 380

Gln Leu Asp Glu Asp Gly Ser Tyr Phe Leu Tyr Ser Lys Leu Ser Val
385                 390                 395                 400

Asp Lys Ser Arg Trp Gln Arg Gly Asp Thr Phe Ile Cys Ala Val Met
                405                 410                 415

His Glu Ala Leu His Asn His Tyr Thr Gln Lys Ser Leu Ser His Ser
                420                 425                 430

Pro Cys Lys
            435
```

What is claimed is:

1. A monoclonal antibody comprising canine and mouse immunoglobulin that specifically binds to canine IgE, wherein the antibody is C15A.2, wherein a nucleotide sequence encoding the antibody comprises SEQ ID NO:6 and SEQ ID NO:7.

* * * * *